US006265194B1

(12) United States Patent
Nezu et al.

(10) Patent No.: US 6,265,194 B1
(45) Date of Patent: Jul. 24, 2001

(54) SERINE-THREONINE KINASE GENE

(75) Inventors: Jun-ichi Nezu; Asuka Oku, both of Ibaraki (JP)

(73) Assignee: Chugai Research Institute for Molecular Medicine, Inc., Ibaraki (JP)

( * ) Notice: Subject to any disclaimer, the term of this patent is extended or adjusted under 35 U.S.C. 154(b) by 0 days.

(21) Appl. No.: 09/344,700

(22) Filed: Jun. 25, 1999

Related U.S. Application Data

(63) Continuation-in-part of application No. PCT/JP97/04855, filed on Dec. 25, 1997.

(30) Foreign Application Priority Data

Dec. 27, 1996 (JP) .................................................. 8-357864

(51) Int. Cl.$^{7}$ .............................. C12N 9/12; C12N 1/20; C12N 15/00; C07H 21/04; C12Q 1/68

(52) U.S. Cl. ........................... 435/194; 435/6; 435/252.3; 435/320.1; 435/325; 536/23.2; 536/24.5

(58) Field of Search ................................. 536/23.2, 24.5; 435/194, 320.1, 252.3, 325, 6

(56) References Cited

U.S. PATENT DOCUMENTS 5,885,803 * 3/1999 Bandman et al. .................. 435/69.1

FOREIGN PATENT DOCUMENTS

98/58052 * 12/1998 (WO) .

OTHER PUBLICATIONS

Zelko et al., Arch. Biochem. Biophys., 352(1), 31–36, Apr. 1998.*

Howard, Susan T., et al.; "Two Early Vaccinia Virus Genes Encode Polypeptides Related to Protein Kinases"; *J. gen. Virol.* (1989), 70, pp 3187–3201.

Lee, Norman H., et al.; "Comparative expressed–sequence–tag analysis of differential gene expression profiles in PC–12 cells before and after nerve growth factor treatment"; (1995) *Proc. Natl. Acad. Sci. USA* vol. 92, pp 8303–8307.

Nezu, Jun–ichi et al.; "Identification of Two Novel Human Putative Serine–Threonine Kinases, VRK1 and VRK2, with Structural Similarity to Vaccinia Virus B1R Kinase"; (1997) *Genomics 45*, pp 327–331.

Smith, Geoffrey L., et al.; "Nucleotide sequence of 42 kbp of vaccinia virus strain WR from near the right inverted terminal repeat"; *Journal of General Virology* (1991), 72, pp 1349–1376.

* cited by examiner

*Primary Examiner*—Rebecca E. Prouty
*Assistant Examiner*—Maryam Monshipouri
(74) *Attorney, Agent, or Firm*—Fish & Richardson P.C.

(57) ABSTRACT

A novel gene having the consensus sequence of a serine-threonine kinase active site has been isolated by the suppression subtractive hybridization method which comprised of preparing a library of genes expressed specifically in fetal livers and isolating clones from this library at random. This gene presumably participates in cell growth control because it is highly expressed, especially in actively growing cells, and exhibits a significant homology with a vaccinia virus B1R kinase gene. Thus, it can be utilized as a target for developing cell growth inhibitors or antitumor agents.

20 Claims, 15 Drawing Sheets

Fig. 1

Adapter 1 5' CTAATACGACTCACTATAGGGCTCGAGCGGCCGCCCGGGCAGGT 3'
3' GGCCCGTCCA 5'

Adapter 2 5' TGTAGCGTGAAGACGACAGAAAGGGCGTGGTGCGGAGGGCGGT 3'
3' GCCTCCCGCCA 5'

Figure 2:
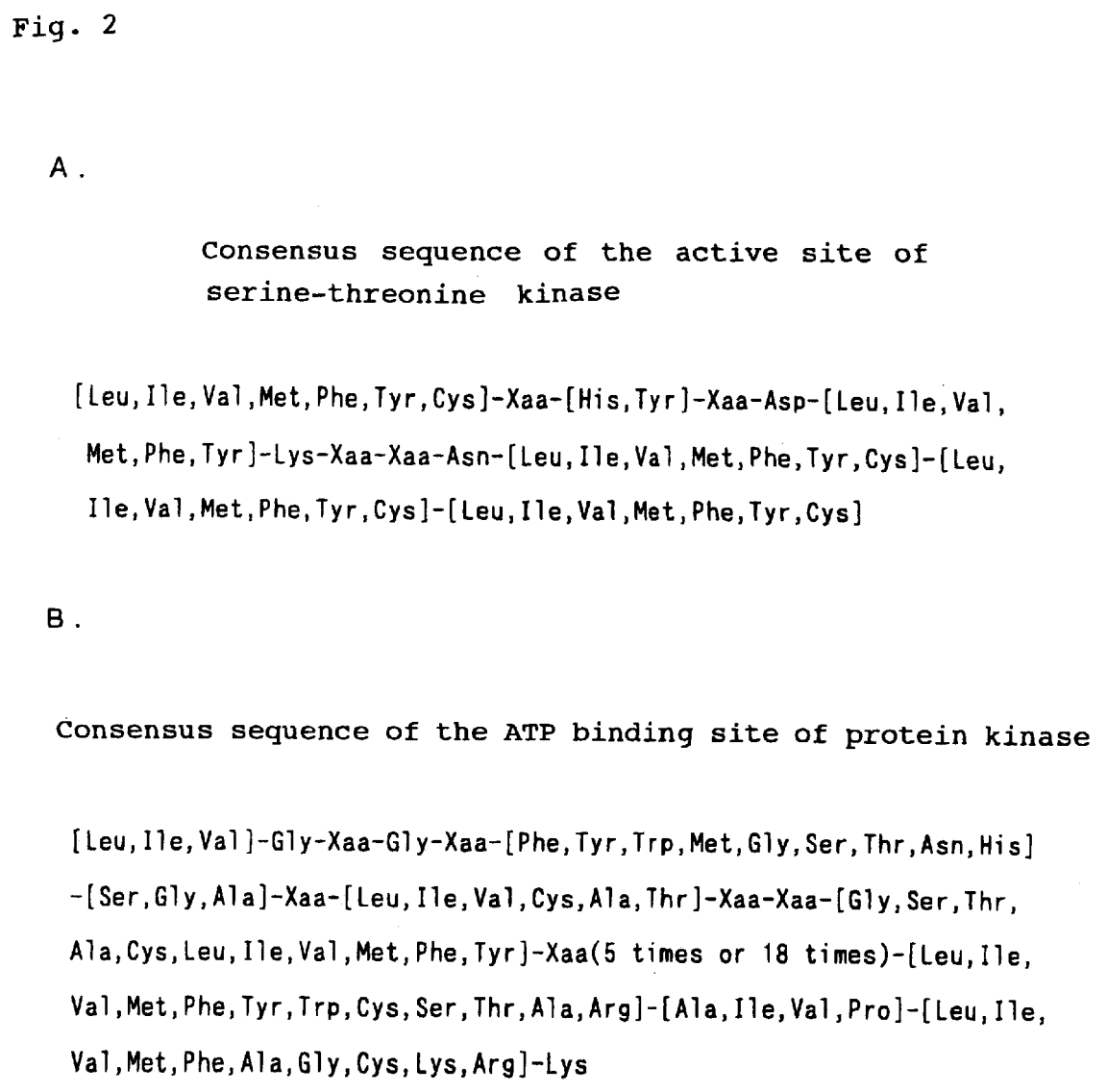

Consensus sequence of the active site of serine-threonine kinase

[Leu,Ile,Val,Met,Phe,Tyr,Cys]-Xaa-[His,Tyr]-Xaa-Asp-[Leu,Ile,Val, Met,Phe,Tyr]-Lys-Xaa-Xaa-Asn-[Leu,Ile,Val,Met,Phe,Tyr,Cys]-[Leu, Ile,Val,Met,Phe,Tyr,Cys]-[Leu,Ile,Val,Met,Phe,Tyr,Cys]

B.

Consensus sequence of the ATP binding site of protein kinase

[Leu,Ile,Val]-Gly-Xaa-Gly-Xaa-[Phe,Tyr,Trp,Met,Gly,Ser,Thr,Asn,His] -[Ser,Gly,Ala]-Xaa-[Leu,Ile,Val,Cys,Ala,Thr]-Xaa-Xaa-[Gly,Ser,Thr, Ala,Cys,Leu,Ile,Val,Met,Phe,Tyr]-Xaa(5 times or 18 times)-[Leu,Ile, Val,Met,Phe,Tyr,Trp,Cys,Ser,Thr,Ala,Arg]-[Ala,Ile,Val,Pro]-[Leu,Ile, Val,Met,Phe,Ala,Gly,Cys,Lys,Arg]-Lys

Fig. 3

```
                9                 18                27                36                45                54
5' ACC TGG GTG TTC CTA AGT ATA GGG GGT CTG GTC TAC ATG ACA AAA ATG GAA AAA
   --- --- --- --- --- --- --- --- --- --- --- --- --- --- --- --- --- ---
   T   W   V   F   L   S   I   G   G   L   V   Y   M   T   K   M   E   K
    P   G   C   S   *   V   *   G   V   W   S   T   *   Q   K   W   K   K
     L   G   V   P   K   Y   R   G   S   G   L   H   D   K   N   G   K   S

                63                72                81                90                99               108
   GTT ACA GGT TTA TGA TAA TGG ATC GCT TTG GGA GTG ACC TTC AGA AAA TAT ATG
   --- --- --- --- --- --- --- --- --- --- --- --- --- --- --- --- --- ---
   V   T   G   L   *   *   W   I   A   L   G   V   T   F   R   K   Y   M
    L   Q   V   Y   D   N   G   S   L   W   E   *   P   S   E   N   I   *
     Y   R   F   M   I   M   D   R   F   G   S   D   L   Q   K   I   Y   E

               117               126               135               144               153               162
   AAG CAA ATG CCA AAA GGT TTT CTC GGA AAA CTG TCT TGC AGC TAA GCT TAA GAA
   --- --- --- --- --- --- --- --- --- --- --- --- --- --- --- --- --- ---
   K   Q   M   P   K   G   F   L   G   K   L   S   C   S   *   A   *   E
    S   K   C   Q   K   V   F   S   E   N   C   L   A   A   K   L   K   N
     A   N   A   K   R   F   S   R   K   T   V   L   Q   L   S   L   R   I

               171               180               189               198               207               216
   TTC TGG ATA TTC TGG AAT ATA TTC ACG AGC ATG AGT ATG TGC ATG GAG ATA TCA
   --- --- --- --- --- --- --- --- --- --- --- --- --- --- --- --- --- ---
   F   W   I   F   W   N   I   F   T   S   M   S   M   C   M   E   I   S
    S   G   Y   S   G   I   Y   S   R   A   *   V   C   A   W   R   Y   Q
     L   D   I   L   E   Y   I   H   E   H   E   Y   V   H   G   D   I   K

               225               234               243               252               261
   AGG CCT CAA ATC TTC TTC TGA ACT ACA AGA ATC CTG ACC AGG TGT 3'
   --- --- --- --- --- --- --- --- --- --- --- --- --- --- ---
   R   P   Q   I   F   F   *   T   T   R   I   L   T   R   C
    G   L   K   S   S   S   E   L   Q   E   S   *   P   G
     A   S   N   L   L   L   N   Y   K   N   P   D   Q   V
```

Fig. 4
Low Middle High Cycle
A F A F A F
G3PDH
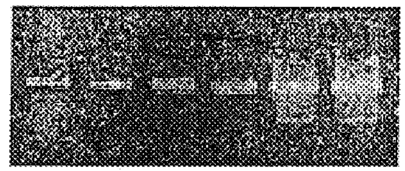
VRK1 (fls223)
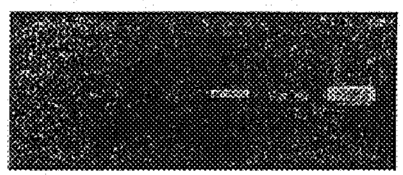
VRK2

Fig. 5

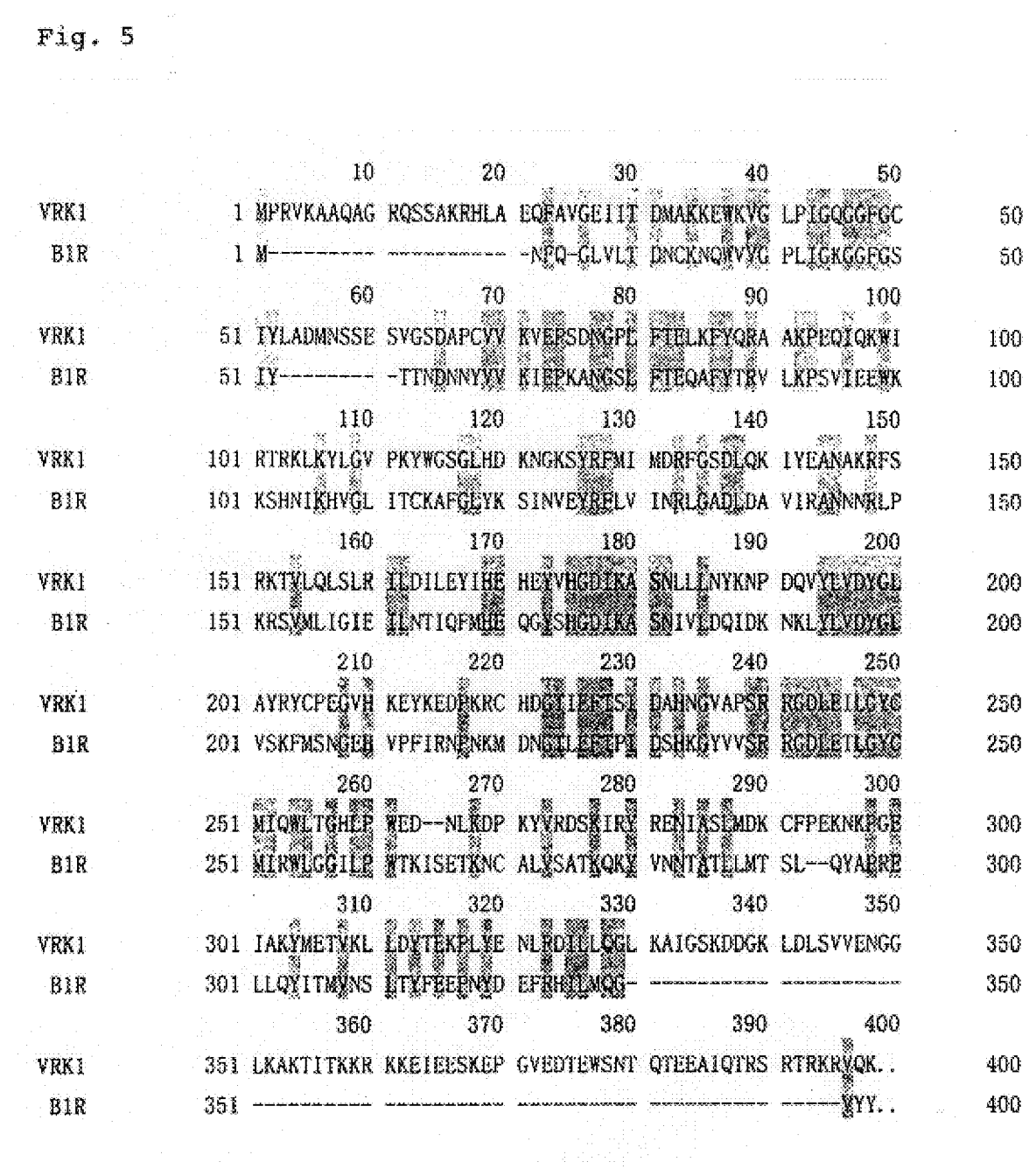

```
                    10         20         30         40         50
VRK1      1 MPRVKAAQAG RQSSAKRHLA EQFAVGEIIT DMAKKEWKVG LPIGQGGFGC     50
 B1R      1 M--------- ---------- -NFQ-GLVLT DNCKNQWVVG PLIGKGGFGS     50
                    60         70         80         90        100
VRK1     51 IYLADMNSSE SVGSDAPCVV KVEPSDNGPL FTELKFYQRA AKPEQIQKWI    100
 B1R     51 IY-------- -TTNDNNYVV KIEPKANGSL FTEQAFYTRV LKPSVIEEWK    100
                   110        120        130        140        150
VRK1    101 RTRKLKYLGV PKYWGSGLHD KNGKSYRFMI MDRFGSDLQK IYEANAKRFS    150
 B1R    101 KSHNIKHVGL ITCKAFGLYK SINVEYRFLV INRLGADLDA VIRANNNRLP    150
                   160        170        180        190        200
VRK1    151 RKTVLQLSLR ILDILEYIHE HEYVHGDIKA SNLLLNYKNP DQVYLVDYGL    200
 B1R    151 KRSVMLIGIE ILNTIQFMHE QGYSHGDIKA SNIVLDQIDK NKLYLVDYGL    200
                   210        220        230        240        250
VRK1    201 AYRYCPEGVH KEYKEDPKRC HDGTIEFTSI DAHNGVAPSR RGDLEILGYC    250
 B1R    201 VSKFMSNGEH VPFIRNPNKM DNGTLEFTPI DSHKGYVVSR RGDLETLGYC    250
                   260        270        280        290        300
VRK1    251 MIQWLTGHLP WED--NLKDP KYVRDSKIRY RENIASLMDK CFPEKNKPGE    300
 B1R    251 MIRWLGGILP WTKISETKNC ALVSATKQKY VNNTATLLMT SL--QYAPRE    300
                   310        320        330        340        350
VRK1    301 IAKYMETVKL LDYTEKPLYE NLRDILLQGL KAIGSKDDGK LDLSVVENGG    350
 B1R    301 LLQYITMVNS LTYFEEPNYD EFRHILMQG- ---------- ----------    350
                   360        370        380        390        400
VRK1    351 LKAKTITKKR KKEIEESKEP GVEDTEWSNT QTEEAIQTRS RTRKRVQK..    400
 B1R    351 ---------- ---------- ---------- ---------- -----VYY..    400
```

Fig. 6

```
                    10         20         30         40         50
VRK1      1 MPRVKAAQAG RQSSAKRHLA EQFAVGEIIT DMAKKEWKVG LPIGQGGFGC      50
VRK2      1 MPP------- -KRNEKYKLP IPFPEGKVLD DMEGNQWVLG KKIGSGGFGL      50
                    60         70         80         90        100
VRK1     51 IYLADMNSSE SVGSDAPCVV KVEPSDNGPL FTELKFYQRA AKPEQIQKWI     100
VRK2     51 IYLA--FPTN KPEKDARHVV KVEYQENGPL FSELKFYQRV AKKDCIKKWI     100
                   110        120        130        140        150
VRK1    101 RTRKLKYLGV PKYWGSGLHD KNGKSYRFMI MDRFGSDLQK IYEANAKRFS     150
VRK2    101 ERKQLDYLGI PLFYGSGLTE FKGRSYRFMV MERLGIDLQK ISGQNGT-FK     150
                   160        170        180        190        200
VRK1    151 RKTVLQLSLR ILDILEYIHE HEYVHGDIKA SNLLLNYKNP DQVYLVDYGL     200
VRK2    151 KSTVLQLGIR MLDVLEYIHE NEYVHGDVKA ANLLLGYKNP DQVYLADYGL     200
                   210        220        230        240        250
VRK1    201 AYRYCPEGVH KEYKEDPKRC HDGTIEFTSI DAHNGVAPSR RGDLEILGYC     250
VRK2    201 SYRYCPNGNH KQYQENPRKG HNGTIEFTSL DAHKGVALSR RSDVEILGYC     250
                   260        270        280        290        300
VRK1    251 MIQWLTGHLP WEDNLKDPKY VRDSKIRYRE NIASLMDKCF PEKNKPGEIA     300
VRK2    251 MLRWLCGKLP WEQNLKDPVA VQTAKTNLLD ELPQSVLKWA PSGSSCCEIA     300
                   310        320        330        340        350
VRK1    301 KYMETVKLLD YTEKPLYENL RDILLQGLKA IGSKDDGKLD LSV-------     350
VRK2    301 QFLVCAHSLA YDEKPNYQAL KKILNPHGIP LGPLDFSTKG QSINVHTPNS     350
                   360        370        380        390        400
VRK1    351 --VENGGLKA KTITKKRKKE IEES--KEPG VED-TEWSNT QTE-------     400
VRK2    351 QKVDSQKAAT KQVNKAHNRL IEKKVHSERS AESCATWKVQ KEEKLIGLMN     400
                   410        420        430        440        450
VRK1    401 -EAIQTRSRT RKRVQK---- ---------- ---------- ----------     450
VRK2    401 NEAAQESTRR RQKYQESQEP LNEVNSFPQK ISYTQFPNSF YEPHQDFTSP     450
                   460        470        480        490        500
VRK1    451 ---------- ---------- ---------- ---------- ----------     500
VRK2    451 DIFKKSRSPS WYKYTSTVST GITDLESSTG LWPTISQFTL SEETNADVYY     500
                   510        520        530        540        550
VRK1    501 ---------- ---------. .......... .......... ..........     550
VRK2    501 YRIIIPVLLM LVFLALFFL. .......... .......... ..........     550
```

Fig. 7

```
                  10         20         30         40         50
VRK2    1 MPPKRNEKYK LPIPFPEGKV LDDMEGNQWV LGKKIGSGGF GLIYLAFPTN    50
B1R     1 MN-------- -----F-QGLV LTDNCKNQWV VGPLIGKGGF GSIY------    50

                  60         70         80         90        100
VRK2   51 KPEKDARHVV KVEYQENGPL FSELKFYQRV AKKDCIKKWI ERKQLDYLGI   100
B1R    51 -TTNDNNYVV KIEPKANGSL FTEQAFYTRV LKPSVIEEFK KSHNIKHVGL   100

                 110        120        130        140        150
VRK2  101 PLFYGSGLTE FKGRSYRFMV MERLGIDLQK -ISGQNGTFK KSTVLQLGIR   150
B1R   101 ITCKAFGLYK SINVEYRFLV INRLGADLDA VIRANNNRLP KRSVMLIGIE   150

                 160        170        180        190        200
VRK2  151 MLDVLEYIHE NEYVHGDVKA ANLLLGYKNP DQVYLADYGL SYRYCPNGNH   200
B1R   151 ILNTIQFMHE QGYSHGDIKA SNIVLDQIDK NKLYLVDYGL VSKFMSNGEH   200

                 210        220        230        240        250
VRK2  201 KQYQENPRKG HNGTIEFTSL DAHKGVALSR RSDVEILGYC MLRWLCGKLP   250
B1R   201 VPFIRNENKM DNGTLEFTPI DSHKGYVVSR RGDLETLGYC MIRWLCGILP   250

                 260        270        280        290        300
VRK2  251 WEQ--NLKDP VAVQTAKTNL LDE---LPQS VLKWAPSGSS CCEIAQFLVC   300
B1R   251 WTKISETKNC ALVSATKQKY VNNTATLLMT SLQYAPR--- --LLLQYITM   300

                 310        320        330        340        350
VRK2  301 AHSLAYDEKP NYQALKKILN PHGIPLGPLD FSTKGQSINV HTPNSQKVDS   350
B1R   301 VNSLTYFEEP NYDEFRHILM Q--------- ---------- ----------   350

                 360        370        380        390        400
VRK2  351 QKAATKQVNK AHNRLIEKKV HSERSAESCA TWKVQKEEKL IGLMNNEAAQ   400
B1R   351 ---------- ---------- ---------- ---------- ----------   400

                 410        420        430        440        450
VRK2  401 ESTRRRQKYQ ESQEPLNEVN SFPQKISYTQ FPNSFYEPHQ DFTSPDIFKK   450
B1R   401 ---------- ---------- ---------- ---------- ----------   450

                 460        470        480        490        500
VRK2  451 SRSPSWYKYT STVSTGITDL ESSTGLWPTI SQFTLSEETN ADVYYYRIII   500
B1R   451 ---------- ---------- ---------- ---------- -GVYY-----   500

                 510        520        530        540        550
VRK2  501 PVLLMLVFLA LFFL...... .......... .......... ..........   550
B1R   501 ---------- ----...... .......... .......... ..........   550
```

1
2
VRK1-myc
50kDa
1. pcDNA3
2. pcDNA3/VRK1myc 1. pCOS
2. pCOS/VRK1w
3. HepG2 pCOS pCOS/VRK1w 1. pGEX/VRK1w
2. pGEX/VRK1K71W

| | | | | | | | | |
|---|---|---|---|---|---|---|---|---|
| histone | + | − | − | − | − | | | |
| casein | − | + | − | − | + | | | |
| MBP | − | − | + | − | − | | | |
| GST | − | − | − | + | − | | | |
| GST-IKB$\alpha$ | | | | | | − | + | + |
| IKB peptide | | | | | | − | − | + |
| wild VRK1 | + | + | + | + | − | + | + | + |
| mutant VRK1 | − | − | − | − | + | − | − | − |

1. ddw
2. 2mM $MgCl_2$
3. 10mM $MgCl_2$
4. 2mM $MnCl_2$
5. 10mM $MnCl_2$
6. 2mM $ZnCl_2$
7. 10mM $ZnCl_2$
8. 2mM $CaCl_2$
9. 10mM $CaCl_2$

SERINE-THREONINE KINASE GENE

This application is a continuation-in-part of International Application PCT/JP97-04855 filed Dec. 25, 1997, which claims priority from Japanese Patent Application No. 8/357864 filed Dec. 27, 1996.

TECHNICAL FIELD

The present invention relates to a novel serine-threonine kinase gene.

BACKGROUND OF ART

Fetal tissues are comprised of many undifferentiated cells that proliferate actively, highly activated cells, nascent vascular endothelial cells, and so on. Although the activity of these cells in fetal tissues is stringently regulated and inhibited as individuals mature, the state of fetal tissues can be considered similar to that of a solid tumor except that the activity is regulated. Therefore, some of the genes expressed specifically or more strongly in fetal tissues (fetal genes) can be genes involved in the phenomena characteristic of solid tumors such as abnormal growth, immortalization, infiltration, metastasis, and angiogenesis. In addition, some diseases other than tumors are also supposed to arise because fetal genes, which are repressed in a normal living body, are abnormally activated. Therefore, genes involved in various diseases such as tumors can be screened by isolating and analyzing fetal genes.

However, there are still few reports on systematic analysis focusing merely on fetal genes from these viewpoints, and at present there is a far from perfect understanding of these gene groups.

DISCLOSURE OF THE INVENTION

An objective of this invention is to isolate genes expressed specifically in fetal tissues and to screen genes related to diseases.

The present inventors thought that fetal tissue cells could be a model for solid tumor cells and that genes involved in diseases such as tumors could be screened by isolating and analyzing fetal genes. Furthermore, the present inventors thought it possible to develop a medicine with a novel action mechanism by designing drugs targeting the genes. Based on these thoughts, the present inventors have tried to isolate fetal genes.

Specifically, the present inventors prepared a subtraction library with many genes expressed specifically in fetal livers (or more strongly than adult livers) by the suppression subtractive hybridization method, extracted clones from this library at random, and analyzed their structure. By doing so, the present inventors succeeded in isolating a novel gene, VRK1, having the consensus sequence of a serine-threonine kinase active site. The present inventors also performed a data base search based on the amino acid sequence deduced from the isolated gene. The present inventors thus have found this gene product exhibits a significant homology with B1R kinase, which is presumably involved in DNA replication of vaccinia virus. In addition, the present inventors found human EST having a very high homology with this gene in the database and isolated its full-length cDNA, VRK2. Analyzing the expression of the two isolated genes in various cells by northern blot analysis showed that these genes are strongly expressed, especially in actively growing cells such as human fetal livers, testes, and various tumor cell lines. Furthermore, the present inventors have found that the VRK1 protein actually has protein kinase activity.

Thus, the present invention relates to novel serine-threonine kinase genes, VRK1 and VRK2. More specifically, the present invention relate to:

(1) a protein having the amino acid sequence of SEQ ID NO: 2, or a protein having the same amino acid sequence where one or more amino acids are added, deleted, or substituted and having serine-threonine kinase activity, (2) a protein having the amino acid sequence of SEQ ID NO: 4, or a protein having the same amino acid sequence where one or more amino acids are added, deleted, or substituted and having serine-threonine kinase activity, (3) a protein encoded by a DNA sequence that hybridizes with the DNA sequence of SEQ ID NO: 1 or its complementary sequence and having serine-threonine kinase activity, (4) a protein encoded by a DNA sequence that hybridizes with the DNA sequence of SEQ ID NO: 3 or its complementary sequence and having serine-threonine kinase activity, (5) a DNA encoding the protein of any one of (1) to (4), (6) a vector comprising the DNA of (5), (7) a transformant carrying the vector of (6), (8) a method of producing the protein of any one of (1) to (4), wherein the method comprises cultivating the transformant of (7), (9) an antibody binding to the protein of any one of (1) to (4),

(10) an antisense DNA against the DNA of (5) or part of it,

(11) a method of screening compounds having inhibitory activity of serine-threonine kinase activity of the protein of any one of (1) to (4), wherein the method is comprised of (a) contacting the protein of any one of (1) to (4) with a substrate to be phosphorylated by this protein in the presence of a test compound to detect the kinase activity of the protein of any one of (1) to (4), and (b) comparing the kinase activity detected in step (a) with that detected in the absence of the test compound and selecting a compound that lowers the kinase activity of the protein of any one of (1) to (4).

The present invention relates to novel serine-threonine kinases, "VRK1" and "VRK2." The nucleotide sequence of the "VRK1" cDNA and the amino acid sequence of the protein are shown in SEQ ID NO: 1 and 2, respectively. In addition, the nucleotide sequence of the "VRK2" cDNA and the amino acid sequence of the protein are shown in SEQ ID NO: 3 and 4, respectively. "VRK1" cDNA has a significant homology with B1R kinase, which is presumably involved in DNA replication of vaccinia virus. The gene is also characterized by its strong expression in actively growing cells such as fetal livers, testes, and various tumor cell lines. In addition, overexpression of "VRK1" protein drastically increases the growing activity of NIH3T3 cells. These facts imply "VRK1" is involved in the regulation mechanism of cell growth. "VRK1" protein has protein kinase activity, which presumably plays an important roll in the regulation of cell growth. "VRK2" has a high homology with "VRK1," especially in the serine-threonine kinase site. "VRK2," like "VRK1," has a significant homology with B1R kinase, and the gene is characterized by its strong expression in actively growing cells such as fetal livers, testes, and various tumor cell lines. These facts imply "VRK2" has the same function as that of "VRK1."

"VRK1" and "VRK2" proteins can be prepared as recombinant proteins with recombinant DNA techniques or as natural proteins. The recombinant proteins can be prepared, for example, by cultivating cells transformed with the DNAs encoding these proteins, as will be described later. Natural proteins can be isolated from fetal livers, testes, or tumor cell strains such as HeLa S3, in which these proteins are highly expressed, by a method well-known to one skilled in the art, such as affinity chromatography with the antibodies of the present invention as described later. Either polyclonal or monoclonal antibodies can be used. The polyclonal antibodies can be prepared from, for example, serum from small animals such as rabbits immunized with these proteins by, for example, ammonium sulfate precipitation, protein A- or protein G-column chromatography, DEAE ion exchange chromatography, affinity chromatography using a column coupled with these proteins, etc. The monoclonal antibodies can be prepared as follows. First, a small animal such as a mouse is immunized with these proteins. The spleen is extracted from the mouse and dissociated to cells. The resulting cells are fused to mouse myeloma cells using a reagent such as polyethylene glycol, and the clone that produces antibodies against these proteins is screened from the fusion cells (hybridoma) thus generated. The hybridoma thus obtained is then transplanted into a mouse abdominal cavity. Ascites is collected from the mouse and purified by, for example, ammonium sulfate precipitation, protein A- or protein G-column chromatography, DEAE ion exchange chromatography, affinity chromatography using a column coupled with "VRK1" or "VRK2" protein, etc. If the antibodies obtained are to be used for administering to a human body (for antibody therapy or the like, etc.), humanized antibodies or human antibodies should be used to decrease immunogenicity. An example of methods for humanizing antibodies is the CDR graft method, in which an antibody gene is cloned from monoclonal antibody-producing cells and its antigenic determinant is transplanted to an existing human antibody. Besides, human antibodies can be directly prepared just like usual monoclonal antibodies by immunizing a mouse whose immune system is replaced with a human immune system.

Furthermore, one skilled in the art can prepare not only natural "VRK1" and "VRK2" proteins (SEQ ID NO: 2 and 4, respectively) but also proteins with substantially the same function as that of the natural proteins, if needed, by replacing amino acids in the proteins by a well-known method. Besides, mutations of amino acids in proteins can occur naturally. Thus, mutant proteins with serine-threonine kinase activity that are generated by introducing amino acid substitution, deletion, or addition into the natural proteins are also included in the proteins of the present invention. Methods for amino acid alteration, for example, a site-directed mutagenesis system using PCR (GIBCO-BRL, Gaithersburg, Md.), the oligonucleotide-mediated site-directed mutagenesis method (Kramer, W. and Fritz, HJ (1987) Methods in Enzymol., 154:350–367), and the Kunkel method (Methods Enzymol. 85, 2763–2766 (1988)), are well-known to one skilled in the art. Furthermore, usually ten or less, preferably six or less, and more preferably three or less amino acids are substituted. For example, proteins functionally equivalent to the VRK1 or VRK2 protein can be produced by conservative amino acid substitutions at one or more amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The site where substitution, deletion, or addition is introduced is not particularly limited as long as the serine-threonine kinase activity is maintained. From the viewpoint of protein activity, the addition, deletion, or substitution of amino acids should be performed in a region other than the region corresponding to the consensus sequence of a serine-threonine kinase active site and to the consensus sequence of a protein kinase ATP binding site. Moreover, serine-threonine kinase activity of a protein can be detected, for example, by the method described in Example 9, mentioned later.

Furthermore, one skilled in the art can usually isolate DNAs having a high homology with the DNA encoding "VRK1" or "VRK2" protein (SEQ ID NO: 1 or 3, respectively) based on the DNA or the part of it using a hybridization technique (Sambrook, J. et al., Molecular Cloning 2nd ed. 9.47–9.58, Cold Spring Harbor Lab. Press, 1989) and obtain proteins having substantially the same function as VRK1 or VRK2 protein (SEQ ID NO: 2 or 4, respectively) from the DNA. Thus, proteins with serine-threonine kinase activity that are encoded by DNAs hybridizing with DNA encoding "VRK1" or "VRK2" protein are also included in the proteins of the present invention. Hybridizing DNAs are isolated from other organisms including, for example, mice, rats, rabbits, and bovines, and so on. Tissues such as fetal livers and testes are especially suitable for isolating. Thus isolated DNAs encoding proteins having substantially the same function as that of "VRK1" or "VRK2" proteins usually have a high homology with the DNA (SEQ ID NO: 1 or 3) encoding "VRK1" or "VRK2" protein, respectively. The term "high homology" used herein means at least 40% or more, preferably 60% or more, and more preferably 80% or more of sequence identity at the amino acid level. From the viewpoint of the protein activity, a high homology should be found in the regions corresponding to the consensus sequence of a serine-threonine kinase active site and to the consensus sequence of a protein kinase ATP binding site.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions)×100). In one embodiment the two sequences are the same length.

To determine percent homology between two sequences, the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877 is used. Such an algorithm is incorporated into the NBLAST and XBLAST programs of Altschul, et al. (1990) *J. Mol. Biol.* 215:403–410. BLAST nucleotide searches are performed with the NBLAST program, score=100, wordlength=12 to obtain nucleotide sequences homologous to a nucleic acid molecules of the invention. BLAST protein searches are performed with the XBLAST program, score=50, wordlength=3 to obtain amino acid sequences homologous to a VRK1 or VRK2 protein molecules. To obtain gapped alignments for comparison purposes, Gapped BLAST is utilized as described in Altschul et al. (1997) *Nucleic Acids Res.* 25:3389–3402. When utilizing BLAST and Gapped BLAST programs, the default parameters of the respective programs (e.g., XBLAST and NBLAST) are used. See http://www.ncbi.nlm.nih.gov.

Furthermore, the present invention relates to a DNA that specifically hybridizes under moderate or highly stringent conditions to a DNA encoding a protein of the present invention and comprises at least 15 nucleotide residues. The DNA can be used, for example, as a probe to detect or isolate a DNA encoding a protein of the present invention, or as a primer for PCR amplification. An example is DNA consisting of at least 15 nucleotides complementary to the nucleotide sequence of SEQ ID NO: 2 or NO: 3.

Standard hybridization conditions (e.g., moderate or highly stringent conditions) are known to those skilled in the art and can be found in *Current Protocols in Molecular Biology,* John Wiley & Sons, N.Y. (1989), 6.3.1–6.3.6, hereby incorporated by reference. Moderate hybridization conditions are defined as equivalent to hybridization in 2×sodium chloride/sodium citrate (SSC) at 30° C., followed by one or more washes in 1×SSC, 0.1% SDS at 50–60° C. Highly stringent conditions are defined as equivalent to hybridization in 6×sodium chloride/sodium citrate (SSC) at 45° C., followed by one or more washes in 0.2×SSC, 0.1% SDS at 50–65° C.

Examples of conditions for hybridization to isolate these DNAs are as follows. After prehybridization at 55° C. for 30 minutes or longer, hybridization is performed by adding labeled probes and incubating at 37° C. to 55° C. for an hour or longer using "ExpressHyb Hybridization Solution" (CLONTECH). After that, the resulting hybridized products are washed three times for 20 minutes each at room temperature in 2×SSC and 0.1% SDS then once at 37° C. in 1×SSC and 0.1% SDS. More preferably, after prehybridization at 60° C. for 30 minutes or longer, hybridization is performed by adding labeled probes and incubating at 60° C. for an hour or longer using "ExpressHyb Hybridization Solution" (CLONTECH). Thereafter, the hybridized products are washed three times for 20 minutes each at room temperature in 2×SSC and 0.1% SDS then twice at 50° C. in 1×SSC and 0.1% SDS. Still more preferably, after prehybridization at 60° C. for 30 minutes or longer, hybridization is performed by adding labeled probes and incubating at 68° C. for an hour or longer using "ExpressHyb Hybridization Solution" (CLONTECH). Thereafter, the hybridized product is are washed three times for 20 minutes each at room temperature in 2×SSC and 0.1% SDS then twice at 50° C. in 0.1×SSC and 0.1% SDS.

The present invention also relates to the DNAs encoding the above-described proteins of the present invention. The DNAs of the present invention include cDNAs, genomic DNAs, and synthetic DNAs as long as they encode the proteins of the present invention. The DNAs of the present invention can be used to produce the recombinant proteins. Specifically, the recombinant proteins can be prepared by inserting the DNA (for example, the DNA of SEQ ID NO: 1 or 3) of the present invention into a suitable expression vector, cultivating the transformant obtained by introducing the vector into suitable cells, and purifying the expressed proteins. For example, mammalian cells such as COS, CHO, or NIH3T3 cells; insect cells such as Sf9 cells; yeast cells; and *E. coli* cells can be used for producing the recombinant proteins. Vectors for expressing recombinant proteins in these cells vary depending on the host cells. For example, pcDNA3 (Invitrogen) or PEF-BOS (Nucleic Acids. Res. 1990, 18(17), p5322) is used for mammalian cells; "BAC-to-BAC baculovirus expression system" (GIBCO BRL), for insect cells; "Pichia Expression Kit" (Invitrogen), for yeast cells; and pGEX-5X-1 (Pharmacia) or "QIAexpress system" (Qiagen), for *E. coli* cells. Vectors can be introduced into host cells by, for example, the method using calcium phosphate, DEAE dextran, or cationic liposome DOTAP (Boehringer Mannheim); electroporation; the calcium chloride method; etc. The recombinant proteins can be purified from the obtained transformants by the usual methods such as the method described in "The Qiaexpressionist handbook, Qiagen, Hilden, Germany."

Furthermore, the DNAs of the present invention can be used for gene therapy of diseases caused by mutations in genomic DNAs. In gene therapy, the DNAs of the present invention are administered to a living body inserted into adenovirus vectors (e.g., pAdexLcw), retrovirus vectors (e.g., pZIPneo) and so on. They can be administered by either ex vivo methods or in vivo methods.

Furthermore, since the proteins of the present invention are presumably involved in the regulation of cell growth, antisense DNAs against the DNAs of the present invention or part of them can be used as inhibitors for developing cell growth or as antitumor agents. The antisense DNAs are administered to a living body directly or in the form of the vectors into which they have been inserted. The antisense DNAs can be synthesized by methods well known to one skilled in the art.

The present invention also relates to a method of screening compounds having inhibitory activity of serine-threonine kinase activity of the proteins of the present invention. This screening method consists of two steps. First, the protein of the present invention is caused to contact a substrate to be phosphorylated by this protein in the presence of a test compound to detect the kinase activity of the protein of the present invention. Second, the kinase activity detected in step (a) is compared with that detected in the absence of the test compound, and a compound that lowers the kinase activity of the protein of the present invention is selected.

Test compounds used for this screening method are not particularly limited and are generally low-molecular-weight compounds, proteins (including the above-described antibodies of the present invention), peptides, etc. Test compounds are either artificially synthesized or natural. Substrates are, for example, casein, IkBα protein, etc. The kinase activity of the protein of the present invention can be detected, for example, by adding ATP having radioactively labeled phosphate to the reaction system containing the protein of the present invention and the substrate and measuring the radioactivity of the phosphate attached to the substrate. Specifically, the activity is detected by the method described in Example 9. The compounds thus isolated can be used as cell growth inhibitors or antitumor agents. Moreover, the present inventors learned that "VRK1" protein phosphorylates IkBα protein. IkBα is thought to be rapidly degraded when phosphorylated, thereby releasing and activating NF-kB bound thereto. In addition, NF-kB is well known as a central transcriptional regulator that causes widespread immune reactions and inflammation reactions. Therefore, compounds that inhibit the kinase activity of the proteins of the present invention can be used as antiphlogistics and immunosuppressants.

BRIEF DESCRIPTION OF THE DRAWING

FIG. 1 shows the adapters used for constructing the subtraction library.

FIGS. 2A–2B shows the consensus sequence of the active site of serine-threonine kinase. FIG. 2B shows the consensus sequence of the ATP binding site of protein kinase.

FIG. 3 shows the nucleotide sequence of the clone fls223 and its deduced amino acid sequences.

FIG. 4 shows electrophoretic patterns demonstrating the result of RT-PCR analysis performed to detect expressions of VRK1 and VRK2 genes in fetal and adult livers. In the figure, "A" and "F" represent Adult liver, and Fetal liver. "Low," "Middle," and "High" represent the level of PCR cycles.

FIG. 5 compares amino acid sequences of VRK1 and B1R.

FIG. 6 compares amino acid sequences of VRK1 and VRK2.

FIG. 7 compares amino acid sequences of VRK2 and B1R.

DETAILED DESCRIPTION THE INVENTION

Figure 8:
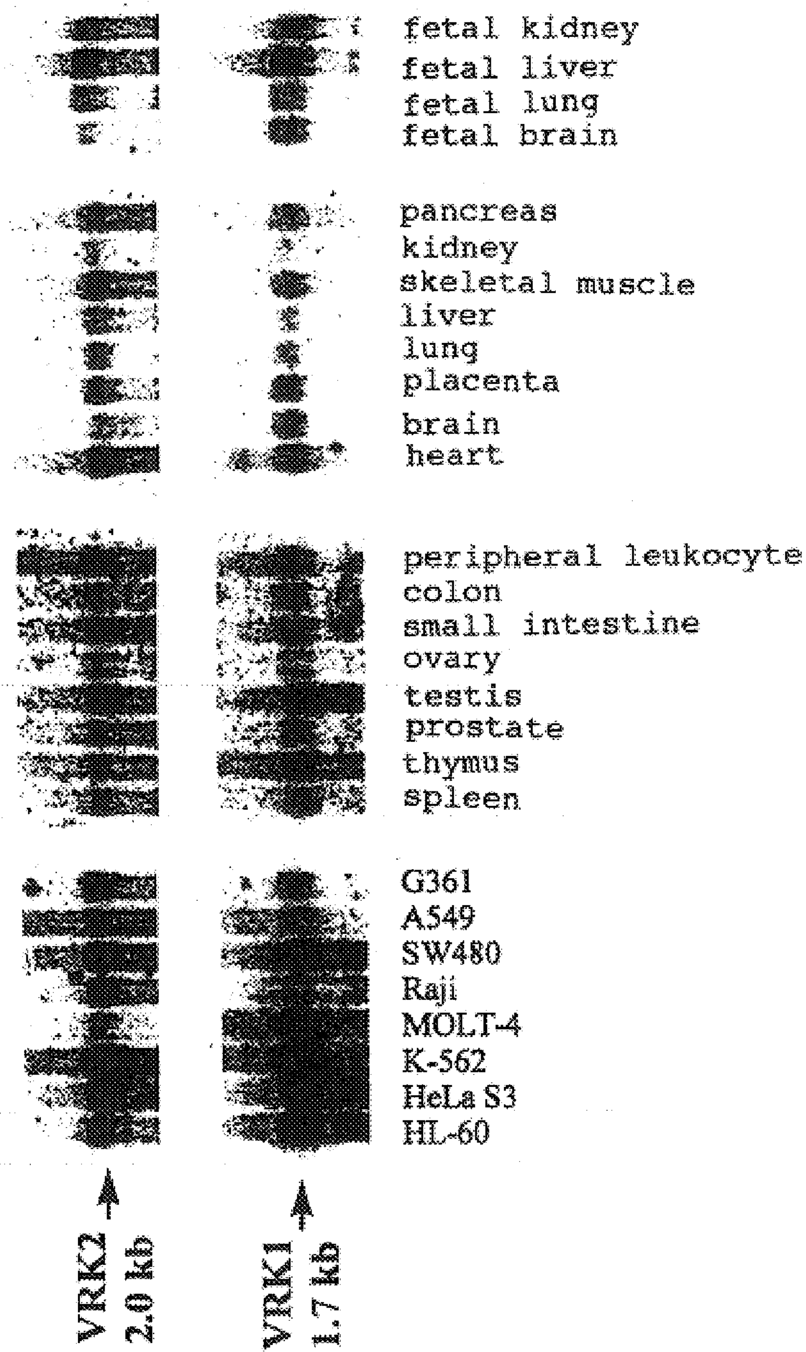
FIG. 8 shows electrophoretic patterns demonstrating the result of northern blot analysis of the expression of VRK1 and VRK2 genes in various cells.

The present invention is illustrated below in detail with reference to examples, but is not to be construed as being limited thereto.

EXAMPLE 1

Construction of a Subtraction Library

A subtraction library was prepared using the PCR-Select™ cDNA Subtraction kit (CLONTECH) basically according to the method described by Luda Diatchenko et al. (Proc. Natl. Acad. Sci. USA, Vol.93, 6025–6030, 1996).

First, double-stranded cDNAs were synthesized from polyA$^+$ RNA prepared from human fetal and adult livers by the standard method using MMLV reverse transcriptase. Next, the respective cDNAs were blunt-ended with T4 DNA polymerase, then cleaved by RsaI. A part of the cDNA originating from fetal liver (tester) was split in two; one of which was ligated with the adapter-1 and the other with the adapter-2 (FIG. 1). Each aliquot was mixed with an excess amount of the adult liver cDNA (driver), denatured by heat, and subjected to the first hybridization at 68° C. for 8 hours. Aliquots were then combined without heat denaturation, mixed further with an excess amount of heat-denatured driver, and subjected to the second hybridization at 68° C. for about 16 hours. The mixture was diluted in the dilution buffer, incubated at 75° C. for 7 minutes to remove the shorter strands of adapters, and used as a template for PCR. By performing PCR with primers corresponding to the adapters, "PCR primer-1" (SEQ ID NO: 5) and "PCR primer-2" (SEQ ID NO: 6), cDNAs carrying different adapters on their two ends (subtracted cDNAs) were selectively amplified (suppression PCR). To obtain products with further selectivity, a portion of the amplified products was used as a template for PCR with primers "Nested PCR primer-1" (SEQ ID NO: 7) and "Nested PCR primer-2" (SEQ ID NO: 8), which locate further inside of the primers; "PCR primer-1" (SEQ ID NO: 5); and "PCR primer-2" (SEQ ID NO: 6). The products were purified using the "QIAquick PCR Purification kit" (QIAGEN), and cloned into the pT7Blue-T vector (Novagen) by the TA cloning method to create a subtraction library.

EXAMPLE 2

Sequence Analysis

Plasmid DNA prepared by the alkali SDS method or products of colony PCR were used as a template for sequence reaction. Sequence reaction was performed by the cycle-sequencing method using the ABI PRISM™ Dye Terminator Cycle Sequencing Ready Reaction Kit With AmplyTaq DNA Polymerase, FS, and the result was analyzed by the ABI 377 DNA Sequencer.

Colony PCR was performed as follows. Colonies carrying recombinant vectors were directly suspended into PCR reaction mixtures that contain vector primers, "M13 P4-22 primer" (SEQ ID NO: 9) and "M13 P5-22 primer" (SEQ ID NO: 10). After PCR reaction, amplified insert DNA was separated from unreacted primers and nucleotides by gel filtration or the like, and used as a template for sequencing.

As a result, the clone fls223 (261 bp) (later renamed "VRK1") was found to be able to encode an amino acid sequence (FIG. 3) that contains the consensus sequence of the active site of serine-threonine kinase ([Leu, Ile, Val, Met, Phe, Tyr, Cys]-Xaa-[His, Tyr]-Xaa-Asp-[Leu, Ile, Val, Met, Phe, Tyr]-Lys-Xaa-Xaa-Asn-[Leu, Ile, Val, Met, Phe, Tyr, Cys, Thr]-[Leu, Ile, Val, Met, Phe, Tyr, Cys, Thr]-[Leu, Ile, Val, Met, Phe, Tyr, Cys, Thr]) (corresponds to amino acids at 173–185 of SEQ ID NO: 2) (FIG. 2A). In addition, no gene registered in the database completely matches the nucleotide sequence of this clone. Thus, the gene is a novel one.

EXAMPLE 3

RT-PCR Assay

Using polyA$^+$ RNA extracted from fetal and adult livers, single-stranded cDNAs were synthesized by the standard method with SUPERSCRIPT™ II RNase H⁻ Reverse Transcriptase (GIBCO BRL). Some of the cDNAs were used as a template for RT-PCR analysis of fls223. PCR was performed using TaKaRa Taq (TaKaRa) as Taq polymerase by the hot-start method, where the reaction was started by adding TaqStart™ Antibody (CLONTECH). Primers "FLS223 S1 primer" (SEQ ID NO: 11) and "FLS223 Al primer" (SEQ ID NO: 12) were used to amplifyfls223.

The G3PDH (glyceraldehyde 3-phosphate dehydrogenase) gene, which is a housekeeping gene equally expressed in various tissues and known to be influenced only slightly by various inducers on its expression, was used as a control. G3PDH was amplified using the primers "hG3PDH5' primer" (SEQ ID NO: 13) and "hG3PDH3' primer" (SEQ ID NO: 14). RT-PCR analysis confirmed that the clone fls223 is strongly expressed in fetal liver, and its expression was also detected in adult liver (FIG. 4). The full-length cDNA was then cloned for more detailed analysis of the gene.

EXAMPLE 4

Cloning by Rapid Amplification of cDNA End (RACE)

The Marathon™ Ready cDNA (CLONTECH) or cDNA prepared by the Marathon™ cDNA Amplification Kit (CLONTECH) was used as a template for 5' RACE and 3' RACE (Chenchik A. et al., CLONTECHniques X, 1, 5–8, 1995).

The primers described above, "FLS223 S1 primer" (SEQ ID NO:. 11) and "FLS223 Al primer" (SEQ ID NO: 12), were used for 5' RACE and 3' RACE of VRK1/fls223. Using a combination of these primers and a primer AP1 (SEQ ID NO: 15), corresponding to the adapter of the template cDNA, the reaction was performed with a combination of these primers and a primer AP1 (SEQ ID NO: 15), corresponding to the adapter of the template cDNAbasically consisted of a reaction at 94° C. for (2 minutes); five cycles of reactions at 94° C. for (30 seconds) and at 68° C. (4 minutes) ; and 30 cycles of reactions at 94° C. for (30 seconds), 62° C. for (1 minute), and 72° C. for (3 minutes;) and followed by a reaction at 72° C. for 10 minutes. TaKaRa Ex Taq (TaKaRa) was used for PCR, and the reaction was started by the hot-start method by adding TaqStart™ Antibody (CLONTECH). After reaction, detected bands were recovered using the QIAquick Gel Extraction Kit (QIAGEN), and subcloned into the pT7Blue-T vector (Novagen).

Analysis of the entire nucleotide sequence revealed that the full-length fls223 cDNA encodes an open reading frame composed of 396 amino acids (refer to SEQ ID NO: 1). In the former part of the amino acid sequence, there exists a consensus sequence of the ATP binding site of protein kinase ([Leu, Ile, Val]-Gly-Xaa-Gly-Xaa-[Phe, Tyr, Trp, Met, Gly, Ser, Thr, Asn, His]-[Ser, Gly, Ala]-Xaa-[Leu, Ile, Val, Cys, Ala, Thr]-Xaa-Xaa-[Gly, Ser, Thr, Ala, Cys, Leu, Ile, Val, Met, Phe, Tyr]-Xaa(five times or 18 times)-[Leu, Ile, Val, Met, Phe, Tyr, Trp, Cys, Ser, Thr, Ala, Arg]-[Ala, Ile, Val, Pro]-[Leu, Ile, Val, Met, Phe, Ala, Gly, Cys, Lys, Arg]-Lys) (corresponds to the amino acids 43–71 described in the SEQ ID NO: 2) (FIG. 2B), and a consensus sequence of the active site of serine-threonine kinase, which is also found in the original clone. Thus, the gene product is assumed to be a novel serine-threonine kinase.

A homology search of the whole database revealed that the gene shows high homology to the B1R gene product of the Vaccinia virus (J. Gen. Virol., 70, 3187–3201, 1989; J. Gen. Virol., 72, 1349–1376, 1991) (FIG. 5). The B1R gene encodes a protein composed of 300 amino acids and is assumed to be a serine-threonine kinase because the gene contains the consensus sequences analogous to that of the ATP binding site of protein kinase and of the active site of serine-threonine kinase. The full-length fls223 cDNA and the B1R gene showed relatively high homology over the entire region as well as in the kinase domain (Smallest Sum probability in Blast search=2.7e–78). Therefore, the gene is named "Vaccinia virus B1R kinase related Kinase 1" (VRK1).

B1R kinase is an early gene whose expression is observed in early stages. It appears several hours after vaccinia virus infection and is then repressed. It has been shown that in a mutant strain containing a point mutation on the gene, virus replication stops during DNA replication. Thus, it has been hypothesized that B1R kinase regulates virus DNA replication (J. Biol. Chem., 264, 21458–21461, 1989).

VRK1 also exhibits an obvious homology to B1R kinase in the region outside of the serine-threonine kinase domain. Thus, VRK1 may participate in the regulation of cellular DNA replication or, more widely, in cell growth control, as is the case for B1R kinase in virus. This notion is supported by the fact that the VRK1 genes are more strongly expressed in tissues such as fetal liver and the testis, where numerous actively growing cells exist.

Furthermore, a public clone "human EST—H80169," which has an extremely high homology to VRK1, was found by searching the data base. Using the primers "RK A2 primer" (SEQ ID NO: 16) and "RK S1 primer" (SEQ ID NO: 17) for 5' RACE and 3' RACE, the full-length cDNA of the gene was cloned as described for VRK1, and the entire nucleotide sequence was determined. As a result, it was found that the gene encodes an open reading frame composed of 508 amino acids (refer to SEQ ID NO: 3), in which the consensus sequence of the active site of serine-threonine kinase exists. Thus, this gene may also encode a novel serine-threonine kinase. The amino acid sequence has an extremely high homology to VRK1, especially near the kinase domain (FIG. 6), and a high homology to the vaccinia virus B1R kinase (FIG. 7). These suggest a close relationship between this kinase and B1R kinase. Thus, it was named "Vaccinia virus B1R kinase related Kinase 2" (VRK2).

RT-PCR confirmed that VRK2 is also expressed more strongly in fetal liver than in adult liver (FIG. 4). The primers "RK S2 primer" (SEQ ID NO: 18) and "RK A2 primer" (SEQ ID NO: 16) were used for RT-PCR.

EXAMPLE 5

Chromosome Mapping

Chromosome mapping of the VRK1 and VRK2 genes was performed using the GENEBRIDGE 4 Radiation Hybrid Panel (Research Genetics, Inc.) (Nature Genetics, 7, 22–28, 1994). DNA on the panel was used as a template for PCR. For VRK1, PCR was performed with a combination of the above primers ("FLS223 S1 primer" (SEQ ID NO: 9) and "FLS223 A1 primer" (SEQ ID NO: 12)) by a reaction at 94° C. for (5 minutes); five cycles of reactions at 94° C. for (30 seconds) and at 72° C. for (2 minutes); and 30 cycles of reactions at 94° C. for (30 seconds) and at 68° C. for (2 minutes; and). This was followed by a reaction at 72° C. for 3 minutes. For VRK2, PCR was performed with a combination of primers "VRK2 A primer" (SEQ ID NO: 19) and "VRK2 B primer" (SEQ ID NO:. 20) by a reaction at 94° C. for (3 minutes);, and 30 cycles of reactions at 94° C. for (30 seconds), 60° C. for (1 minute), and 72° C. for (2 minutes; and). This was followed by a reaction at 72° C. for 5 minutes. The resulting pattern was analyzed on a database on Internet (http://www-genome.wi.mit.edu/cgi-bin/contig/rhmapper.pl), and maps were obtained.

The VRK1 gene was thus mapped to the position between the STS markers "D14S265" and "AFM063XE7" on chromosome 14. Similarly, the VRK2 gene was mapped to the position between the STS markers "CHLC.GATA23H01" and "D2S357" on chromosome 2.

EXAMPLE 6

Northern Blot Analysis

The expressions of VRK1 and VRK2 mRNA in various human normal tissues and tumor cell lines were analyzed by northern blotting (FIG. 8).

The 5' terminal fragment of the VRK1 cDNA (upstream region of the HindIII site at nucleotide residue 546) or that of the VRK2 cDNA (upstream region of the EcoRI site at position 426) was labeled with [$\alpha$-$^{32}$P]dCTP by the random primer method using Ready-to-Go DNA labeling beads (Pharmacia), and used as a probe. Hybridization was performed at 68° C. in ExpressHyb Hybridization Solution (CLONTECH) using Multiple Tissue Northern (MTN) Blot—Human, Human II, Human Fetal II, and Human Cell line (CLONTECH) according to the method recommended by the manufacturer. Final wash was done at 50° C. in 0.1×SSC, 0.1% SDS, and the image on the filter processed through hybridization was analyzed with the BAS-2000II bioimaging analyzer (Fuji Photo Film).

In FIG. 8, tumor cell lines used are malignant melanoma cells "G361," lung carcinoma cells "A549," colorectal adenocarcinoma cells "SW480," Burkitt's lymphoma cells "Raji," acute lymphoblastic leukemia cells (T cell) "MOLT-4," chronic myelogenous leukemia cells "K-562," uterocervical carcinoma cells "HeLaS3," and promyelocytic leukemia cells "HL60".

The results revealed that VRK1 was expressed relatively highly in fetal tissues, and extremely highly in fetal liver. VRK1 was expressed weakly in almost all adult tissues, but it was expressed strongly in the testis and the thymus. In tumor cell lines, a very strong expression of VRK1 was observed in six out of eight cell lines.

The expression pattern of VRK2 was basically similar to that of VRK1; VRK2 was expressed strongly in fetal liver and the testis. Similarly, it was expressed strongly in tumor cell lines. However, VRK2 was not expressed in MOLT-4 cells, in contrast to the pattern of VRK1 MRNA.

EXAMPLE 7

Constructing Expression Plasmid DNAs

CDNA containing the entire coding region of VRK1 or VRK2 was amplified by PCR using a combination of primers, VRK1 S1 primer (SEQ ID NO: 21) and VRK1 A1 primer (SEQ ID NO: 22), or VRK2 S1 primer (SEQ ID NO: 23) and VRK2 A1 primer (SEQ ID NO: 24) from CDNA synthesized from polyA$^+$ RNA extracted from human fetal liver. The amplified product was cleaved at the NotI site that is attached to the end of the primers and purified by agarose gel electrophoresis to obtain DNA fragments of the correct size. These were subcloned into the PCOS vector, which was pretreated with NotI and dephosphorylated on its ends with alkaline-phosphatase/CIAP (TaKaRa). This vector contains an EF1$\alpha$ promoter and enables expressing cloned CDNA strongly in a broad range of mammalian cell lines. By sequencing the thus-obtained subclones, clones (PCOS/VRK1w, PCOS/VRK2w) without mutation such as PCR error were selected and used for expression as described below and for further construction of expression plasmid DNA.

Plasmids for expressing proteins in which the anti c-Myc antibody epitope sequence (SEQ ID NO: 25) is attached to the C-terminus were constructed as follows. Using about 50 nanograms of the plasmid DNA and with PCOS/VRK1w or PCOS/VRK2w as a template, PCR was performed with a combination of primers. These included VRK1 MYC1 primer (SEQ ID NO: 26) and VRK1 MYC2 primer (SEQ ID NO: 27), or VRK2 MYC1 primer (SEQ ID NO: 28) and VRK2 MYC2 primer (SEQ ID NO: 29), and CDNA with the anti c-Myc antibody epitope attached to the C-terminus of the coding sequence was amplified. KOD DNA polymerase (TOYOBO) was used as the DNA polymerase. The amplified product was cleaved at the BamHI site that is attached to the end of the primers and purified by agarose gel electrophoresis to obtain DNA fragments of the correct size. These were subcloned into the pcdna3 vector (Invitrogen), which was digested with BamHI and dephosphorylated on its ends with alkaline-phosphatase/CIAP (TaKaRa). By sequencing the thus-obtained subclones, clones (pcdna3/VRK1myc, pcdna3/VRK2myc) without mutation such as PCR error were selected, and used for later experiments.

Expression plasmid DNAs for glutathione-S-transferase (GST) fusion proteins in *E. coli* were constructed as follows. Using the plasmid DNA PCOS/VRK1w or PCOS/VRK2w as a template, the coding region was amplified by PCR with a combination of primers, VRK1 H3 primer (SEQ ID NO: 30) and VRK1 H4 primer (SEQ ID NO: 31), or VRK2 H3 primer (SEQ ID NO: 32) and VRK2 H4 primer (SEQ ID NO: 33). The amplified product was cleaved at the BamHI site that is attached to the end of the primers purified by agarose gel electrophoresis to obtain DNA fragments of the correct size. These were then subcloned into the PGEX-5X-1 vector (Pharmacia), which was digested with BamHI and dephosphorylated on its ends with alkaline-phosphatase/CIAP (TaKaRa). By sequencing the thus-obtained subclones, clones (PGEX/VRK1w, PGEX/VRK2w) without mutation such as PCR error were selected and used for later experiments.

A clone with a mutation introduced to the predicted ATP binding site within the kinase catalytic domain (Lys at position 71 in the amino acid sequence of SEQ ID NO: 2 is replaced by Trp) was constructed using the Chameleon™ Double-Stranded Site-Directed Mutagenesis Kit (STRATAGENE) as follows. About one microgram of the PGEX/VRK1w plasmid DNA was mixed with primers VRK1 KW1 primer (SEQ ID NO: 34) and a selection primer, Select1 primer (SEQ ID NO: 35), and heat denatured by boiling for 5 minutes. Plasmid DNA and both primers containing mutation were then annealed by incubating at room temperature for 30 minutes. Next, new DNA strands were synthesized from primers by adding substrate nucleotides, DNA polymerase, etc. These were treated with PstI to digest wild plasmid DNA, and introduced into XLmutS competent cells. After overnight liquid culture, plasmid DNA was extracted then treated with PstI to digest contaminating wild plasmid DNA. It was then reintroduced into the competent cells. By sequencing several single isolated colonies, a clone (PGEX/VRK1K71W) with an introduced mutation was selected.

EXAMPLE 8

Expression in Mammalian Cell Lines

Figure 9:
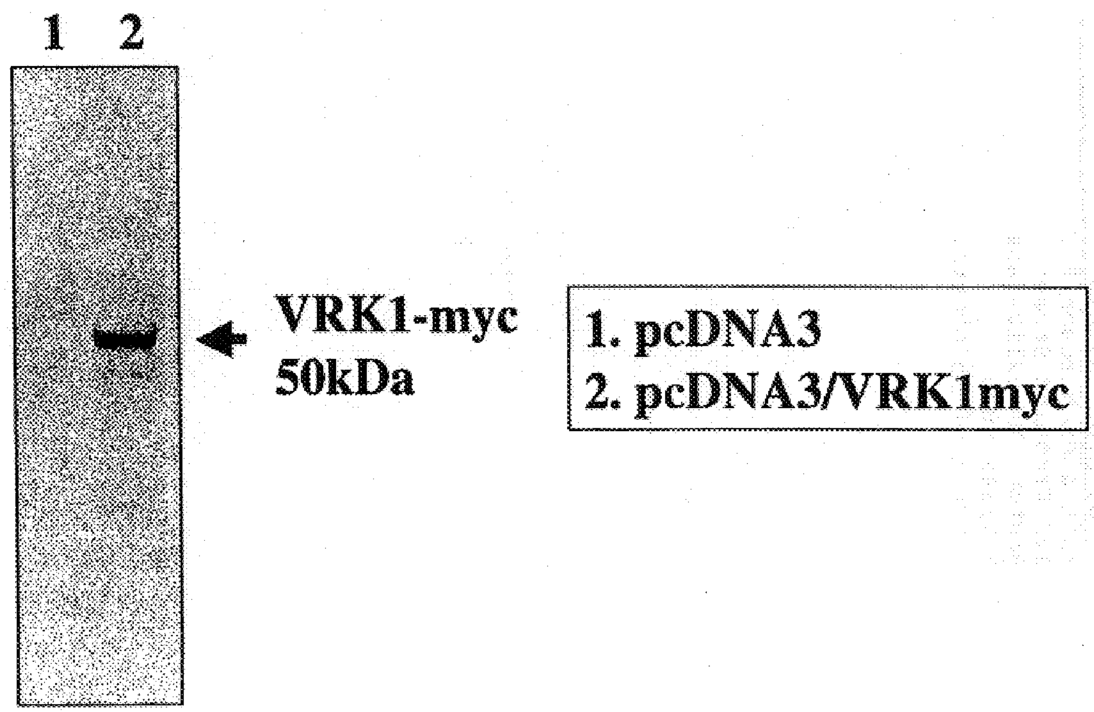
FIG. 9 shows an electrophoretic pattern demonstrating the result of western blot analysis using anti c-Myc antibody. Cell extracts from COS7 cells transfected with plasmid DNA, pcDNA3 (lane 1) or pcDNA3/VRK1myc (lane 2), were examined.

About 10 micrograms of plasmid DNA, pcdna3/VRK1myc or pcdna3, was introduced (transfected) into COS7 cells using SuperFect (QIAGEN). Specifically, about $10^6$ COS7 cells were plated in a 10-cm dish, and cultured overnight. A mixture of 10 micrograms of plasmid DNA and 60 microliters of SuperFect was then added to the culture, and the culture was incubated for about 3 hours. Thereafter, the culture medium was replaced with fresh medium. The cells were then cultured for two more days and collected by detaching in a trypsin-EDTA solution. Cells were washed once in PBS, disrupted in RIPA buffer (1% NP-40, 10 Mm Tris-Hcl (Ph 7.2), 0.1% sodium deoxychorate, 0.1% SDS, 0.15 M sodium chloride, 1 Mm EDTA, 10 micrograms/ml aprotinin, 1 Mm PMSF), and cell extracts were obtained by centrifugation. The cell extracts were separated by SDS-polyacrylamide gel electrophoresis (SDS-PAGE) and subjected to western blot analysis using anti c-Myc antibody (SANTA CRUZ). A band of about 50 kDa was specifically observed in cells transfected with the pcdna3/VRK1myc plasmid DNA, indicating that VRK1myc protein is expressed (FIG. 9).

Figure 10:
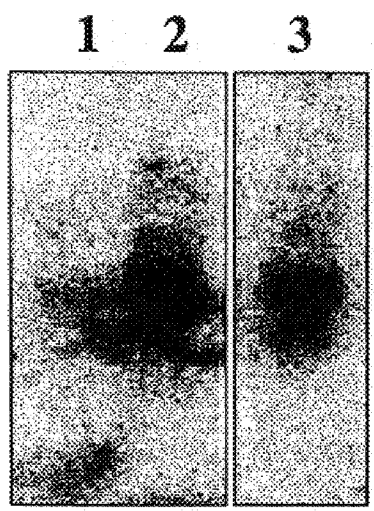
FIG. 10 shows an electrophoretic pattern demonstrating the result of northern blot analysis using the VRK1 cDNA as a probe. Total RNA samples prepared from NIH3T3 cells transfected with plasmid DNA, pCOS (lane 1) or pCOS/VRK1w (lane 2), and from a human hepatoma cell line, HepG2 cells (lane 3), were examined.
Figure 11:
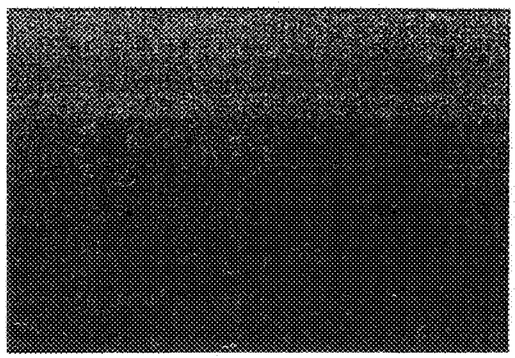
FIG. 11 presents microscopic photographs showing the result of colony assay. A pool of NIH3T3 cells transfected with plasmid DNA, pCOS ("pCOS") or pCOS/VRK1w ("PCOS/VRK1w") was examined.

Next, about 7.5 micrograms of plasmid DNA, PCOS/VRK1w or PCOS, was transfected into NIH3T3 cells by the method using cationic phospholipid DOTAP (Boehringer Mannheim). After transfection, transformants were selected by adding G418 (GIBCO-BRL) to the culture medium to a final concentration of 500 micrograms/ml. Total RNA was prepared from each pool of transformants by the method using ISOGEN (Wako Junyaku). The total RNA was then subjected to northern blot analysis using the VRK1 CDNA as a probe. The results confirmed that VRK1 MRNA was expressed in a pool of cells obtained by transfection with the PCOS/VRK1w plasmid DNA (FIG. 10). These pools of cells were examined for the ability to form colonies on soft agar (colony assay). To this end, $2\times10^4$ cells were suspended in Dulbecco's Modified Eagle Medium (DMEM) containing 10% fetal bovine serum and 0.4% thawed SeaPlaque agarose (TaKaRa), and overlaid on a bottom agarose, which was made of 0.53% SeaPlaque agarose, 10% fetal bovine serum, and DMEM. After two-week culturing, the pool of cells obtained by transfection with the PCOS/VRK1w plasmid DNA formed a number of colonies that were obviously larger than those formed in the pool of cells obtained by transfection with the PCOS plasmid DNA. This suggests that overexpression of VRK1 confers abnormal growth activities on cells (FIG. 11).

EXAMPLE 9

Expression of VRK1 Protein in *E. coli* and Kinase Assay

Figure 12:
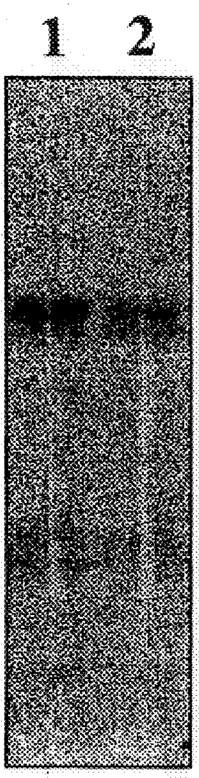
FIG. 12 shows an electrophoretic pattern of purified GST fusion proteins (CBB staining). Fusion proteins with wild VRK1 protein (lane 1) or with a mutant one (lane 2) were examined.

Both wild VRK1 protein and mutant VRK1 protein were expressed in *E. coli* as a fusion protein with GST protein and purified. The *E. coli* DH5α strain cells carrying the above-described plasmid DNA, PGEX/VRK1w, or PGEX/VRK1K71W were cultured overnight at 37° C. in 10 ml 2×YT medium. Some of the culture was diluted 100-fold with fresh 2×YT medium and cultured at 37° C. until the OD value at 600 nm reached 0.6. IPTG (isopropyl-β-D(−)-thiogalactopyranoside) was then added to the culture to a final concentration of 0.1 Mm, and the culture was incubated further for several hours. The *E. coli* cells were collected by centrifugation, resuspended in PBS containing 1% Triton X-100 and 1% Tween 20, and subsequently disrupted by sonication to solubilize proteins. From the solubilized samples, wild VRK1 protein and mutant VRK1, which were expressed as a fusion protein with GST, were purified by affinity chromatography using glutathione Sepharose4B (Pharmacia). These proteins were subjected to SDS-PAGE and stained with Coomassie Brilliant Blue (CBB) to confirm their purity (FIG. 12). GST protein and GST-IkBα protein were prepared in the same manner.

Kinase assay was performed on a total of 50 microliters of a reaction mixture containing 0.2 micrograms of wild or mutant VRK1 protein, 50 Mm Tris-Hcl (Ph 7.2), 1 Mm dithiothreitol (DTT), 2 Mm or 10 Mm of divalent cation (Mg, Mn, Zn, Ca), a maximum of 5 micrograms of substrate protein, and 1 microliter of [$\gamma$-$^{32}$P]-ATP (3000 Ci/Mm, 10 mCi/ml [Amersham]). In some experiments, another buffer system containing 40 Mm Hepes (Ph 7.4), 1 Mm DTT, and 2.5 Mm EGTA was used.

Figure 13:
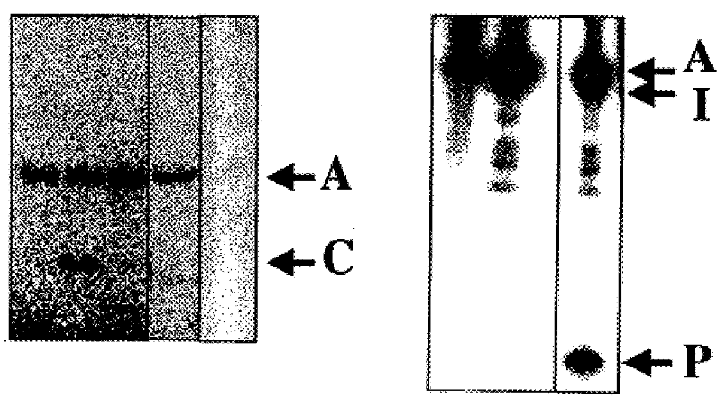
FIG. 13 shows electrophoretic patterns demonstrating the result of kinase assay. Added proteins are indicated by "+" on the upper portion. Arrows indicate phosphorylated GST-VRK1 ("A," autophosphorylation), phosphorylated casein ("C"), phosphorylated GST-IkBα ("I"), and phosphorylated IkBα C-terminal peptide ("P").

Specifically, the reaction was first performed in the presence of 10 Mm Mg at 37° C. for 30 minutes using, as a protein substrate, histone (Nakalai), casein (Sigma), myelin basic protein/MBP (Sigma), GST, GST-IkBα, or IkBα C-terminal peptide (SEQ ID NO: 36). The reaction mixture was subjected to SDS-PAGE, and the radioactivity of phosphorylated proteins was analyzed with a BAS2000II bioimaging analyzer (Fuji Photo Film). The result indicates that wild VRK1 protein phosphorylates casein and GST-IkBα (FIG. 13). In contrast, no phosphorylation was observed in reactions with mutant VRK1 carrying mutation in the predicted ATP binding site. This indicates that VRK1 is a protein kinase that contains a typical catalytic domain. In addition, GST protein was not phosphorylated by VRK1, suggesting that the phosphorylation of GST-IkBα protein by VRK1 occurs within IkBα protein but not in GST moiety.

IkBα is said to negatively regulate the function of transcription factor NF-Kb by forming a complex with it. In addition, it is widely accepted that IkBα is inactivated by self-phosphorylation, immediately thereafter undergoes proteolysis, thereby liberating and activating NF-Kb. NF-Kb is supposed to be a central transcriptional regulator that induces a broad range of immune reactions and inflammatory reactions. Therefore, a kinase that phosphorylates IkBα is important as a target molecule of anti-inflammatory drugs. Since VRK1 strongly phosphorylates IkBα in vitro, VRK1 probably participates in the activation of NF-Kb by phosphorylating IkBα in vivo as well. Therefore, it is possible to anticipate anti-inflammatory effects or immunosuppressive effects by inhibiting VRK1 kinase activity, or by reducing its protein amount.

Figure 14:
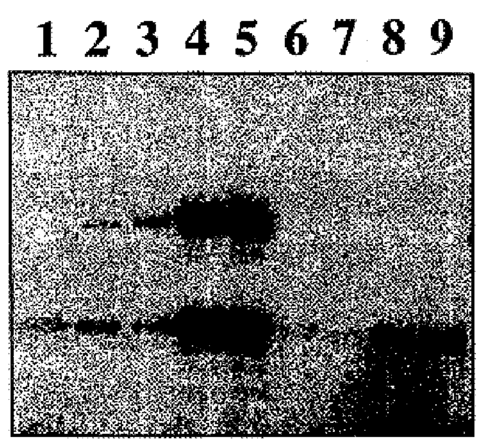
FIG. 14 shows an electrophoretic pattern demonstrating the result of kinase assay. Reactions were performed in the presence of various divalent cations at various concentrations as indicated on the right. Arrows indicate phosphorylated GST-VRK1 ("A," autophosphorylation), and phosphorylated casein ("C").

Next, the requirement for divalent cations in phosphorylation by VRK1 was examined (FIG. 14). In the presence of various divalent cations (Mg, Mn, Zn, and Ca) at a final concentration of 2 Mm or 10 Mm, kinase reactions were performed using casein as a substrate protein. The result showed that VRK1 exhibits phosphorylation activity in the presence of all divalent cations except for Zn. However, the levels of activity were different; VRK1 exhibited especially strong activity in the presence of Mn.

EXAMPLE 10

Preparation of an antibody against VRK1 protein

Figure 15:
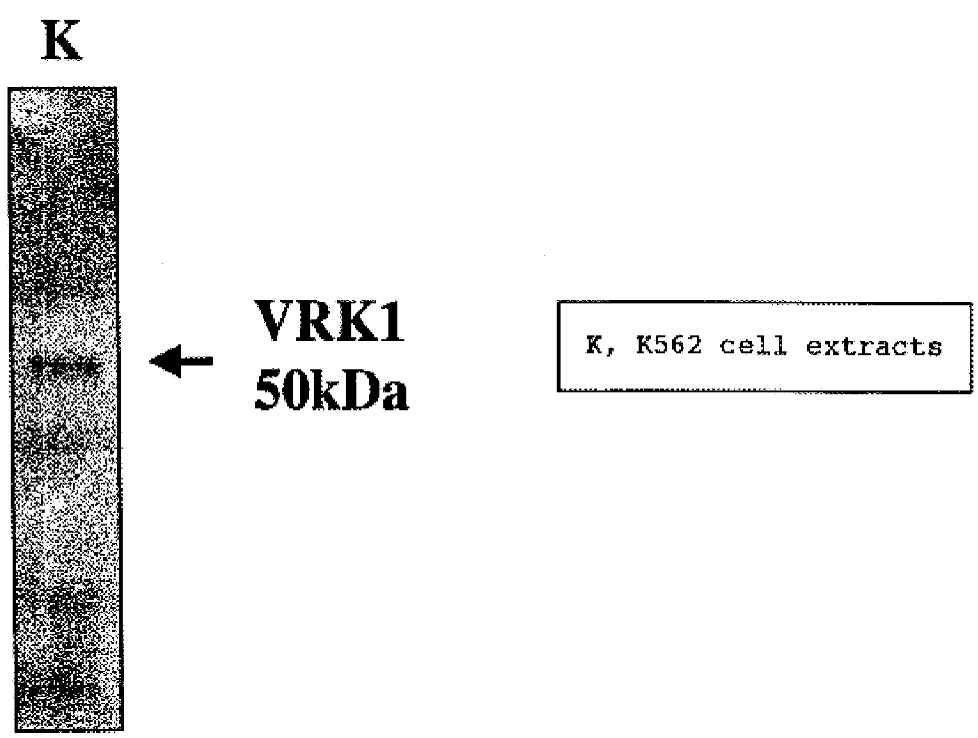
FIG. 15 shows an electrophoretic pattern demonstrating the result of western blot analysis with an antibody against a VRK1 peptide using K562 cell extracts.

A peptide (SEQ ID NO: 37) corresponding to the C-terminal sequence of the deduced VRK1 amino acid sequence was synthesized (Sawady Technology) and conjugated to Keyhole limpet hemocyanin (KLH) at its amino-terminal cysteine mediated by m-maleimidobenzoyl-N-hydroxy-succinimide ester (MBS). This was used as an antigen to immunize rabbits, and antisera were obtained. Antibodies that specifically react with the peptide were purified from the antisera by affinity chromatography using Cellulofine (Seikagaku Corporation) conjugated with the peptide. Western blot analysis using extracts of K562 cells, which were confirmed by northern blot analysis to strongly express VRK1, detected a single band with a molecular weight of approximately 50 Kda, indicating that VRK1 protein is specifically recognized by the antibody (FIG. 15).

INDUSTRIAL APPLICABILITY

The serine-threonine kinase genes isolated by the present inventors show significant homology to a vaccinia virus gene that is thought to be involved in DNA replication and are strongly expressed in actively growing cells. Furthermore, overexpression of proteins encoded by the genes remarkably enhances cell proliferation activity. Thus, the isolated serine-threonine kinase genes are assumed to participate in the regulation of cell growth. Therefore, it is possible to develop cell growth inhibitors or antitumor agents based on a novel mechanism by screening drugs targeted on the genes (such as antisense DNA), or drugs which can regulate either the expression of the genes or the activity of the proteins encoded by the genes of the present invention.

What is claimed is:

1. An isolated DNA encoding a polypeptide comprising the amino acid sequence of SEQ ID NO:2 or 4.

2. An isolated DNA comprising the nucleotide sequence of SEQ ID NO:1 or 3.

3. An isolated DNA encoding a polypeptide comprising an amino acid sequence that is at least 80% identical to SEQ ID NO:2 or 4, wherein the polypeptide is a serine-threonine kinase.

4. An isolated DNA that hybridizes to a nucleic acid consisting of the nucleotide sequence of SEQ ID NO:1 or 3, wherein the hybridization is performed at 50° C. and in 0.1×SSC and 0.1% SDS, and wherein the isolated DNA encodes a serine-threonine kinase.

5. A vector comprising the isolated DNA of claim 1.

6. A vector comprising the isolated DNA of claim 2.

7. A vector comprising the isolated DNA of claim 3.

8. A vector comprising the isolated DNA of claim 4.

9. A transformed cell comprising the vector of claim 5.

10. A transformed cell comprising the vector of claim 6.

11. A transformed cell comprising the vector of claim 7.

12. A transformed cell comprising the vector of claim 8.

13. A method of producing a polypeptide, the method comprising culturing the transformed cell of claim 9, and expressing the polypeptide in the cell.

14. A method of producing a polypeptide, the method comprising culturing the transformed cell of claim 10, and expressing the polypeptide in the cell.

15. A method of producing a polypeptide, the method comprising culturing the transformed cell of claim 11, and expressing the polypeptide in the cell.

16. A method of producing a polypeptide, the method comprising culturing the transformed cell of claim 12, and expressing the polypeptide in the cell.

17. An antisense DNA fully complementary to a mRNA encoding a serine-threonine kinase comprising the amino acid sequence of SEQ ID NO:2 or 4, wherein the antisense DNA inhibits the production of the serine-threonine kinase.

18. An antisense DNA fully complementary to a mRNA encoding a serine-threonine kinase and comprising the RNA-equivalent nucleotide sequence of SEQ ID NO:1 or 3, wherein the antisense DNA inhibits the production of the serine-threonine kinase.

19. An antisense DNA fully complementary to a mRNA encoding a serine-threonine kinase comprising an amino acid sequence that is at least 80% identical to SEQ ID NO:2 or 4, wherein the antisense DNA inhibits the production of the serine-threonine kinase.

20. An antisense DNA fully complementary to a mRNA encoding a serine-threonine kinase, wherein the mRNA hybridizes to a nucleic acid consisting of the nucleotide sequence of SEQ ID NO:1 or 3, the hybridization being performed at 50° C. and in 0.1×SSC and 0.1% SDS, and wherein the antisense DNA inhibits the production of the serine-threonine kinase.

* * * * *

UNITED STATES PATENT AND TRADEMARK OFFICE

CERTIFICATE OF CORRECTION

PATENT NO. : 6,265,194 B1
DATED : July 24, 2001
INVENTOR(S) : Asuka Oku and Jun-ichi Nezu It is certified that error appears in the above-identified patent and that said Letters Patent is hereby corrected as shown below:

Column 2,
Line 3, "relate" should be -- relates --.

Column 5,
Line 52, delete the word "are".

Column 6,
Line 4, "PEF" should be -- pEF --.

Column 7,
Line 5, delete "–2B".
Line 63, "DETAILED DESCRIPTION THE INVENTION" should be -- DETAILED DESCRIPTION OF THE INVENTION --.

Column 9,
Line 34, insert a space after "cDNA".

Column 35, line 36, and Column 36, line 49,
"50ºC." should be -- "50ºC" -- (without period).

Signed and Sealed this

Fourth Day of June, 2002

*Attest:*

JAMES E. ROGAN

*Attesting Officer* *Director of the United States Patent and Trademark Office*

SEQUENCE LISTING

```
<160> NUMBER OF SEQ ID NOS: 37

<210> SEQ ID NO 1
<211> LENGTH: 1662
<212> TYPE: DNA
<213> ORGANISM: Homo sapiens
<220> FEATURE:
<221> NAME/KEY: CDS
<222> LOCATION: (76)...(1263)

<400> SEQUENCE: 1

ccgagttacg agtcggcgaa agcggcggga agttcgtact gggcagaacg cgacgggtct      60

gcggcttagg tgaaa atg cct cgt gta aaa gca gct caa gct gga aga cag     111
                 Met Pro Arg Val Lys Ala Ala Gln Ala Gly Arg Gln
                  1               5                  10

agc tct gca aag aga cat ctt gca gaa caa ttt gca gtt gga gag ata     159
Ser Ser Ala Lys Arg His Leu Ala Glu Gln Phe Ala Val Gly Glu Ile
         15                  20                  25

ata act gac atg gca aaa aag gaa tgg aaa gta gga tta ccc att ggc     207
Ile Thr Asp Met Ala Lys Lys Glu Trp Lys Val Gly Leu Pro Ile Gly
     30                  35                  40

caa gga ggc ttt ggc tgt ata tat ctt gct gat atg aat tct tca gag     255
Gln Gly Gly Phe Gly Cys Ile Tyr Leu Ala Asp Met Asn Ser Ser Glu
 45                  50                  55                  60

tca gtt ggc agt gat gca cct tgt gtt gta aaa gtg gaa ccc agt gac     303
Ser Val Gly Ser Asp Ala Pro Cys Val Val Lys Val Glu Pro Ser Asp
                 65                  70                  75

aat gga cct ctt ttt act gaa tta aag ttc tac caa cga gct gca aaa     351
Asn Gly Pro Leu Phe Thr Glu Leu Lys Phe Tyr Gln Arg Ala Ala Lys
             80                  85                  90

cca gag caa att cag aaa tgg att cgt acc cgt aag ctg aag tac ctg     399
Pro Glu Gln Ile Gln Lys Trp Ile Arg Thr Arg Lys Leu Lys Tyr Leu
         95                 100                 105

ggt gtt cct aag tat tgg ggg tct ggt cta cat gac aaa aat gga aaa     447
Gly Val Pro Lys Tyr Trp Gly Ser Gly Leu His Asp Lys Asn Gly Lys
    110                 115                 120

agt tac agg ttt atg ata atg gat cgc ttt ggg agt gac ctt cag aaa     495
Ser Tyr Arg Phe Met Ile Met Asp Arg Phe Gly Ser Asp Leu Gln Lys
125                 130                 135                 140

ata tat gaa gca aat gcc aaa agg ttt tct cgg aaa act gtc ttg cag     543
Ile Tyr Glu Ala Asn Ala Lys Arg Phe Ser Arg Lys Thr Val Leu Gln
                145                 150                 155

cta agc tta aga att ctg gat att ctg gaa tat att cac gag cat gag     591
Leu Ser Leu Arg Ile Leu Asp Ile Leu Glu Tyr Ile His Glu His Glu
            160                 165                 170

tat gtg cat gga gat atc aag gcc tca aat ctt ctt ctg aac tac aag     639
Tyr Val His Gly Asp Ile Lys Ala Ser Asn Leu Leu Leu Asn Tyr Lys
        175                 180                 185

aat cct gac cag gtg tac ttg gta gat tat ggc ctt gct tat cgg tac     687
Asn Pro Asp Gln Val Tyr Leu Val Asp Tyr Gly Leu Ala Tyr Arg Tyr
    190                 195                 200
```

-continued

```
tgc cca gaa gga gtt cat aaa gaa tac aaa gaa gac ccc aaa aga tgt      735
Cys Pro Glu Gly Val His Lys Glu Tyr Lys Glu Asp Pro Lys Arg Cys
205                 210                 215                 220

cac gat ggc act att gaa ttc acg agc atc gat gca cac aat ggt gtg      783
His Asp Gly Thr Ile Glu Phe Thr Ser Ile Asp Ala His Asn Gly Val
                225                 230                 235

gcc cca tca aga cgt ggt gat ttg gaa ata ctt ggt tat tgc atg atc      831
Ala Pro Ser Arg Arg Gly Asp Leu Glu Ile Leu Gly Tyr Cys Met Ile
            240                 245                 250

caa tgg ctt act ggc cat ctt cct tgg gag gat aat ttg aaa gat cct      879
Gln Trp Leu Thr Gly His Leu Pro Trp Glu Asp Asn Leu Lys Asp Pro
        255                 260                 265

aaa tat gtt aga gat tcc aaa att aga tac aga gaa aat att gca agt      927
Lys Tyr Val Arg Asp Ser Lys Ile Arg Tyr Arg Glu Asn Ile Ala Ser
    270                 275                 280

ttg atg gac aaa tgt ttt cct gag aaa aac aaa cca ggt gaa att gcc      975
Leu Met Asp Lys Cys Phe Pro Glu Lys Asn Lys Pro Gly Glu Ile Ala
285                 290                 295                 300

aaa tac atg gaa aca gtg aaa tta cta gac tac act gaa aaa cct ctt     1023
Lys Tyr Met Glu Thr Val Lys Leu Leu Asp Tyr Thr Glu Lys Pro Leu
                305                 310                 315

tat gaa aat tta cgt gac att ctt ttg caa gga cta aaa gct ata gga     1071
Tyr Glu Asn Leu Arg Asp Ile Leu Leu Gln Gly Leu Lys Ala Ile Gly
            320                 325                 330

agt aag gat gat ggc aaa ttg gac ctc agt gtt gtg gag aat gga ggt     1119
Ser Lys Asp Asp Gly Lys Leu Asp Leu Ser Val Val Glu Asn Gly Gly
        335                 340                 345

ttg aaa gca aaa aca ata aca aag aag cga aag aaa gaa att gaa gaa     1167
Leu Lys Ala Lys Thr Ile Thr Lys Lys Arg Lys Lys Glu Ile Glu Glu
    350                 355                 360

agc aag gaa cct ggt gtt gaa gat acg gaa tgg tca aac aca cag aca     1215
Ser Lys Glu Pro Gly Val Glu Asp Thr Glu Trp Ser Asn Thr Gln Thr
365                 370                 375                 380

gag gag gcc ata cag acc cgt tca aga acc aga aag aga gtc cag aag     1263
Glu Glu Ala Ile Gln Thr Arg Ser Arg Thr Arg Lys Arg Val Gln Lys
                385                 390                 395

taattcagat gctgtgaacc agatttcctt ttctttgttt tcttttgact tttttctcct   1323

tttctgttag aactgtttta ttttcctgtg agtcttgcga ggtggaatta atgattaaat   1383

actcatgtgt tcagaaaaca taaacttttt ttataaaaat attttgtaca attcattaaa   1443

ggctaattta tgaaatttga aaatcttcag gttatactcc ttaagttatc ccaaagccgt   1503

gtgtttgtga tgttttggag tacatatata tgaaaattat tatgacacgc acttttctaa   1563

tcattgtaca tttctcagag tggataaaaa tgtttgacaa agtcctcact tttaaggaaa   1623

tgcaaagctt aaaataaaac tctcttttgt ttgatgcag                          1662


<210> SEQ ID NO 2
<211> LENGTH: 396
<212> TYPE: PRT
<213> ORGANISM: Homo sapiens

<400> SEQUENCE: 2

Met Pro Arg Val Lys Ala Ala Gln Ala Gly Arg Gln Ser Ser Ala Lys
 1               5                  10                  15

Arg His Leu Ala Glu Gln Phe Ala Val Gly Glu Ile Ile Thr Asp Met
            20                  25                  30

Ala Lys Lys Glu Trp Lys Val Gly Leu Pro Ile Gly Gln Gly Gly Phe
        35                  40                  45
```

-continued

```
Gly Cys Ile Tyr Leu Ala Asp Met Asn Ser Ser Glu Ser Val Gly Ser
    50                  55                  60

Asp Ala Pro Cys Val Val Lys Val Glu Pro Ser Asp Asn Gly Pro Leu
65                  70                  75                  80

Phe Thr Glu Leu Lys Phe Tyr Gln Arg Ala Ala Lys Pro Glu Gln Ile
                85                  90                  95

Gln Lys Trp Ile Arg Thr Arg Lys Leu Lys Tyr Leu Gly Val Pro Lys
            100                 105                 110

Tyr Trp Gly Ser Gly Leu His Asp Lys Asn Gly Lys Ser Tyr Arg Phe
        115                 120                 125

Met Ile Met Asp Arg Phe Gly Ser Asp Leu Gln Lys Ile Tyr Glu Ala
    130                 135                 140

Asn Ala Lys Arg Phe Ser Arg Lys Thr Val Leu Gln Leu Ser Leu Arg
145                 150                 155                 160

Ile Leu Asp Ile Leu Glu Tyr Ile His Glu His Glu Tyr Val His Gly
                165                 170                 175

Asp Ile Lys Ala Ser Asn Leu Leu Leu Asn Tyr Lys Asn Pro Asp Gln
            180                 185                 190

Val Tyr Leu Val Asp Tyr Gly Leu Ala Tyr Arg Tyr Cys Pro Glu Gly
        195                 200                 205

Val His Lys Glu Tyr Lys Glu Asp Pro Lys Arg Cys His Asp Gly Thr
    210                 215                 220

Ile Glu Phe Thr Ser Ile Asp Ala His Asn Gly Val Ala Pro Ser Arg
225                 230                 235                 240

Arg Gly Asp Leu Glu Ile Leu Gly Tyr Cys Met Ile Gln Trp Leu Thr
                245                 250                 255

Gly His Leu Pro Trp Glu Asp Asn Leu Lys Asp Pro Lys Tyr Val Arg
            260                 265                 270

Asp Ser Lys Ile Arg Tyr Arg Glu Asn Ile Ala Ser Leu Met Asp Lys
        275                 280                 285

Cys Phe Pro Glu Lys Asn Lys Pro Gly Glu Ile Ala Lys Tyr Met Glu
    290                 295                 300

Thr Val Lys Leu Leu Asp Tyr Thr Glu Lys Pro Leu Tyr Glu Asn Leu
305                 310                 315                 320

Arg Asp Ile Leu Leu Gln Gly Leu Lys Ala Ile Gly Ser Lys Asp Asp
                325                 330                 335

Gly Lys Leu Asp Leu Ser Val Val Glu Asn Gly Gly Leu Lys Ala Lys
            340                 345                 350

Thr Ile Thr Lys Lys Arg Lys Lys Glu Ile Glu Glu Ser Lys Glu Pro
        355                 360                 365

Gly Val Glu Asp Thr Glu Trp Ser Asn Thr Gln Thr Glu Glu Ala Ile
    370                 375                 380

Gln Thr Arg Ser Arg Thr Arg Lys Arg Val Gln Lys
385                 390                 395
```

```
<210> SEQ ID NO 3
<211> LENGTH: 1833
<212> TYPE: DNA
<213> ORGANISM: Homo sapiens
<220> FEATURE:
<221> NAME/KEY: CDS
<222> LOCATION: (131)...(1654)

<400> SEQUENCE: 3

ctgcactgcg aggccgacgc agctggagag aagttaggca ggtcctaggg agggcaggct     60
```

-continued

```
cgagtgctgg gcccgcctcc ccgcgggact gtaggcccgg gggctccgcc tcgtcgcagc    120

ggcagaagtg atg cca cca aaa aga aat gaa aaa tac aaa ctt cct att      169
           Met Pro Pro Lys Arg Asn Glu Lys Tyr Lys Leu Pro Ile
             1               5                  10

cca ttt cca gaa ggc aag gtt ctg gat gat atg gaa ggc aat cag tgg      217
Pro Phe Pro Glu Gly Lys Val Leu Asp Asp Met Glu Gly Asn Gln Trp
     15                  20                  25

gta ctg ggc aag aag att ggc tct gga gga ttt gga ttg ata tat tta      265
Val Leu Gly Lys Lys Ile Gly Ser Gly Gly Phe Gly Leu Ile Tyr Leu
 30                  35                  40                  45

gct ttc ccc aca aat aaa cca gag aaa gat gca aga cat gta gta aaa      313
Ala Phe Pro Thr Asn Lys Pro Glu Lys Asp Ala Arg His Val Val Lys
                 50                  55                  60

gtg gaa tat caa gaa aat ggc ccg tta ttt tca gaa ctt aaa ttt tat      361
Val Glu Tyr Gln Glu Asn Gly Pro Leu Phe Ser Glu Leu Lys Phe Tyr
             65                  70                  75

cag aga gtt gca aaa aaa gac tgt atc aaa aag tgg ata gaa cgc aaa      409
Gln Arg Val Ala Lys Lys Asp Cys Ile Lys Lys Trp Ile Glu Arg Lys
         80                  85                  90

caa ctt gat tat tta gga att cct ctg ttt tat gga tct ggt ctg act      457
Gln Leu Asp Tyr Leu Gly Ile Pro Leu Phe Tyr Gly Ser Gly Leu Thr
     95                 100                 105

gaa ttc aag gga aga agt tac aga ttt atg gta atg gaa aga cta gga      505
Glu Phe Lys Gly Arg Ser Tyr Arg Phe Met Val Met Glu Arg Leu Gly
110                 115                 120                 125

ata gat tta cag aag atc tca ggc cag aat ggt acc ttt aaa aag tca      553
Ile Asp Leu Gln Lys Ile Ser Gly Gln Asn Gly Thr Phe Lys Lys Ser
                130                 135                 140

act gtc ctg caa tta ggt atc cga atg ttg gat gta ctg gaa tat ata      601
Thr Val Leu Gln Leu Gly Ile Arg Met Leu Asp Val Leu Glu Tyr Ile
            145                 150                 155

cat gaa aat gaa tat gtt cat ggt gat gta aaa gca gca aat cta ctt      649
His Glu Asn Glu Tyr Val His Gly Asp Val Lys Ala Ala Asn Leu Leu
        160                 165                 170

ttg ggt tac aaa aat cca gac cag gtt tat ctt gca gat tat gga ctt      697
Leu Gly Tyr Lys Asn Pro Asp Gln Val Tyr Leu Ala Asp Tyr Gly Leu
    175                 180                 185

tcc tac aga tat tgt ccc aat ggg aac cac aaa cag tat cag gaa aat      745
Ser Tyr Arg Tyr Cys Pro Asn Gly Asn His Lys Gln Tyr Gln Glu Asn
190                 195                 200                 205

cct aga aaa ggc cat aat ggg aca ata gag ttt acc agc ttg gat gcc      793
Pro Arg Lys Gly His Asn Gly Thr Ile Glu Phe Thr Ser Leu Asp Ala
                210                 215                 220

cac aag gga gta gcc ttg tcc aga cga agt gac gtt gag atc ctc ggc      841
His Lys Gly Val Ala Leu Ser Arg Arg Ser Asp Val Glu Ile Leu Gly
            225                 230                 235

tac tgc atg ctg cgg tgg ttg tgt ggg aaa ctt ccc tgg gaa cag aac      889
Tyr Cys Met Leu Arg Trp Leu Cys Gly Lys Leu Pro Trp Glu Gln Asn
        240                 245                 250

ctg aag gac cct gtg gct gtg cag act gct aaa aca aat ctg ttg gac      937
Leu Lys Asp Pro Val Ala Val Gln Thr Ala Lys Thr Asn Leu Leu Asp
    255                 260                 265

gag ctc ccc cag tca gtg ctt aaa tgg gct cct tct gga agc agt tgc      985
Glu Leu Pro Gln Ser Val Leu Lys Trp Ala Pro Ser Gly Ser Ser Cys
270                 275                 280                 285

tgt gaa ata gcc caa ttt ttg gta tgt gct cat agt tta gca tat gat     1033
Cys Glu Ile Ala Gln Phe Leu Val Cys Ala His Ser Leu Ala Tyr Asp
                290                 295                 300
```

-continued

```
gaa aag cca aac tat caa gcc ctc aag aaa att ttg aac cct cat gga      1081
Glu Lys Pro Asn Tyr Gln Ala Leu Lys Lys Ile Leu Asn Pro His Gly
            305                 310                 315

ata cct tta gga cca ctg gac ttt tcc aca aaa gga cag agt ata aat      1129
Ile Pro Leu Gly Pro Leu Asp Phe Ser Thr Lys Gly Gln Ser Ile Asn
        320                 325                 330

gtc cat act cca aac agt caa aaa gtt gat tca caa aag gct gca aca      1177
Val His Thr Pro Asn Ser Gln Lys Val Asp Ser Gln Lys Ala Ala Thr
    335                 340                 345

aag caa gtc aac aag gca cac aat agg tta atc gaa aaa aaa gtc cac      1225
Lys Gln Val Asn Lys Ala His Asn Arg Leu Ile Glu Lys Lys Val His
350                 355                 360                 365

agt gag aga agc gct gag tcc tgt gca aca tgg aaa gtg cag aaa gag      1273
Ser Glu Arg Ser Ala Glu Ser Cys Ala Thr Trp Lys Val Gln Lys Glu
                370                 375                 380

gag aaa ctg att gga ttg atg aac aat gaa gca gct cag gaa agc aca      1321
Glu Lys Leu Ile Gly Leu Met Asn Asn Glu Ala Ala Gln Glu Ser Thr
            385                 390                 395

agg aga aga cag aaa tat caa gag tct caa gaa cct ttg aat gaa gta      1369
Arg Arg Arg Gln Lys Tyr Gln Glu Ser Gln Glu Pro Leu Asn Glu Val
        400                 405                 410

aac agt ttc cca caa aaa atc agc tat aca caa ttc cca aac tca ttt      1417
Asn Ser Phe Pro Gln Lys Ile Ser Tyr Thr Gln Phe Pro Asn Ser Phe
    415                 420                 425

tat gag cct cat caa gat ttt acc agt cca gat ata ttc aag aag tca      1465
Tyr Glu Pro His Gln Asp Phe Thr Ser Pro Asp Ile Phe Lys Lys Ser
430                 435                 440                 445

aga tct cca tct tgg tat aaa tac act tcc aca gtc agc acg ggg atc      1513
Arg Ser Pro Ser Trp Tyr Lys Tyr Thr Ser Thr Val Ser Thr Gly Ile
                450                 455                 460

aca gac tta gaa agt tca act gga ctt tgg cct aca att tcc cag ttt      1561
Thr Asp Leu Glu Ser Ser Thr Gly Leu Trp Pro Thr Ile Ser Gln Phe
            465                 470                 475

act ctt agt gaa gag aca aac gca gat gtt tat tat tat cgc atc atc      1609
Thr Leu Ser Glu Glu Thr Asn Ala Asp Val Tyr Tyr Tyr Arg Ile Ile
        480                 485                 490

ata cct gtc ctt ttg atg tta gta ttt ctt gct tta ttt ttt ctc          1654
Ile Pro Val Leu Leu Met Leu Val Phe Leu Ala Leu Phe Phe Leu
    495                 500                 505

tgaagatgat accaaaattc cttttgataa ttttttaagt ttccagctct tcaccgaaat   1714

gttgtattct tatttcagtg tttccttcca gacattttta aggtaattgg ctttaaaaag   1774

agaacatatt ttaacaaagt ttgtggacac tctaaaaaat aaaattgctt tgtactagt    1833


<210> SEQ ID NO 4
<211> LENGTH: 508
<212> TYPE: PRT
<213> ORGANISM: Homo sapiens

<400> SEQUENCE: 4

Met Pro Pro Lys Arg Asn Glu Lys Tyr Lys Leu Pro Ile Pro Phe Pro
 1               5                  10                  15

Glu Gly Lys Val Leu Asp Asp Met Glu Gly Asn Gln Trp Val Leu Gly
            20                  25                  30

Lys Lys Ile Gly Ser Gly Gly Phe Gly Leu Ile Tyr Leu Ala Phe Pro
        35                  40                  45

Thr Asn Lys Pro Glu Lys Asp Ala Arg His Val Val Lys Val Glu Tyr
    50                  55                  60

Gln Glu Asn Gly Pro Leu Phe Ser Glu Leu Lys Phe Tyr Gln Arg Val
```

-continued

```
65                  70                  75                  80

Ala Lys Lys Asp Cys Ile Lys Lys Trp Ile Glu Arg Lys Gln Leu Asp
                85                  90                  95

Tyr Leu Gly Ile Pro Leu Phe Tyr Gly Ser Gly Leu Thr Glu Phe Lys
            100                 105                 110

Gly Arg Ser Tyr Arg Phe Met Val Met Glu Arg Leu Gly Ile Asp Leu
        115                 120                 125

Gln Lys Ile Ser Gly Gln Asn Gly Thr Phe Lys Lys Ser Thr Val Leu
    130                 135                 140

Gln Leu Gly Ile Arg Met Leu Asp Val Leu Glu Tyr Ile His Glu Asn
145                 150                 155                 160

Glu Tyr Val His Gly Asp Val Lys Ala Ala Asn Leu Leu Leu Gly Tyr
                165                 170                 175

Lys Asn Pro Asp Gln Val Tyr Leu Ala Asp Tyr Gly Leu Ser Tyr Arg
            180                 185                 190

Tyr Cys Pro Asn Gly Asn His Lys Gln Tyr Gln Glu Asn Pro Arg Lys
        195                 200                 205

Gly His Asn Gly Thr Ile Glu Phe Thr Ser Leu Asp Ala His Lys Gly
    210                 215                 220

Val Ala Leu Ser Arg Arg Ser Asp Val Glu Ile Leu Gly Tyr Cys Met
225                 230                 235                 240

Leu Arg Trp Leu Cys Gly Lys Leu Pro Trp Glu Gln Asn Leu Lys Asp
                245                 250                 255

Pro Val Ala Val Gln Thr Ala Lys Thr Asn Leu Leu Asp Glu Leu Pro
            260                 265                 270

Gln Ser Val Leu Lys Trp Ala Pro Ser Gly Ser Ser Cys Cys Glu Ile
        275                 280                 285

Ala Gln Phe Leu Val Cys Ala His Ser Leu Ala Tyr Asp Glu Lys Pro
    290                 295                 300

Asn Tyr Gln Ala Leu Lys Lys Ile Leu Asn Pro His Gly Ile Pro Leu
305                 310                 315                 320

Gly Pro Leu Asp Phe Ser Thr Lys Gly Gln Ser Ile Asn Val His Thr
                325                 330                 335

Pro Asn Ser Gln Lys Val Asp Ser Gln Lys Ala Ala Thr Lys Gln Val
            340                 345                 350

Asn Lys Ala His Asn Arg Leu Ile Glu Lys Lys Val His Ser Glu Arg
        355                 360                 365

Ser Ala Glu Ser Cys Ala Thr Trp Lys Val Gln Lys Glu Glu Lys Leu
    370                 375                 380

Ile Gly Leu Met Asn Asn Glu Ala Ala Gln Glu Ser Thr Arg Arg Arg
385                 390                 395                 400

Gln Lys Tyr Gln Glu Ser Gln Glu Pro Leu Asn Glu Val Asn Ser Phe
                405                 410                 415

Pro Gln Lys Ile Ser Tyr Thr Gln Phe Pro Asn Ser Phe Tyr Glu Pro
            420                 425                 430

His Gln Asp Phe Thr Ser Pro Asp Ile Phe Lys Lys Ser Arg Ser Pro
        435                 440                 445

Ser Trp Tyr Lys Tyr Thr Ser Thr Val Ser Thr Gly Ile Thr Asp Leu
    450                 455                 460

Glu Ser Ser Thr Gly Leu Trp Pro Thr Ile Ser Gln Phe Thr Leu Ser
465                 470                 475                 480

Glu Glu Thr Asn Ala Asp Val Tyr Tyr Tyr Arg Ile Ile Ile Pro Val
                485                 490                 495
```

-continued

```
Leu Leu Met Leu Val Phe Leu Ala Leu Phe Phe Leu
            500                 505


<210> SEQ ID NO 5
<211> LENGTH: 22
<212> TYPE: DNA
<213> ORGANISM: Homo sapiens

<400> SEQUENCE: 5

ctaatacgac tcactatagg gc                                      22


<210> SEQ ID NO 6
<211> LENGTH: 21
<212> TYPE: DNA
<213> ORGANISM: Homo sapiens

<400> SEQUENCE: 6

tgtagcgtga agacgacaga a                                       21


<210> SEQ ID NO 7
<211> LENGTH: 22
<212> TYPE: DNA
<213> ORGANISM: Homo sapiens

<400> SEQUENCE: 7

tcgagcggcc gcccgggcag gt                                      22


<210> SEQ ID NO 8
<211> LENGTH: 22
<212> TYPE: DNA
<213> ORGANISM: Homo sapiens

<400> SEQUENCE: 8

agggcgtggt gcggagggcg gt                                      22


<210> SEQ ID NO 9
<211> LENGTH: 22
<212> TYPE: DNA
<213> ORGANISM: Homo sapiens

<400> SEQUENCE: 9

ccagggtttt cccagtcacg ac                                      22


<210> SEQ ID NO 10
<211> LENGTH: 22
<212> TYPE: DNA
<213> ORGANISM: Homo sapiens

<400> SEQUENCE: 10

tcacacagga aacagctatg ac                                      22


<210> SEQ ID NO 11
<211> LENGTH: 24
<212> TYPE: DNA
<213> ORGANISM: Homo sapiens

<400> SEQUENCE: 11

tgtagttcag aagaagattt gagg                                    24


<210> SEQ ID NO 12
<211> LENGTH: 24
<212> TYPE: DNA
<213> ORGANISM: Homo sapiens
```

-continued

<400> SEQUENCE: 12
ataatggatc gctttgggag tgac 24

<210> SEQ ID NO 13
<211> LENGTH: 26
<212> TYPE: DNA
<213> ORGANISM: Homo sapiens

<400> SEQUENCE: 13
tgaaggtcgg agtcaacgga tttggt 26

<210> SEQ ID NO 14
<211> LENGTH: 24
<212> TYPE: DNA
<213> ORGANISM: Homo sapiens

<400> SEQUENCE: 14
catgtgggcc atgaggtcca ccac 24

<210> SEQ ID NO 15
<211> LENGTH: 27
<212> TYPE: DNA
<213> ORGANISM: Homo sapiens

<400> SEQUENCE: 15
ccatcctaat acgactcact atagggc 27

<210> SEQ ID NO 16
<211> LENGTH: 24
<212> TYPE: DNA
<213> ORGANISM: Homo sapiens

<400> SEQUENCE: 16
ggattttcct gatactgttt gtgg 24

<210> SEQ ID NO 17
<211> LENGTH: 24
<212> TYPE: DNA
<213> ORGANISM: Homo sapiens

<400> SEQUENCE: 17
accacaaaca gtatcaggaa aatc 24

<210> SEQ ID NO 18
<211> LENGTH: 24
<212> TYPE: DNA
<213> ORGANISM: Homo sapiens

<400> SEQUENCE: 18
acctttaaaa agtcaactgt cctg 24

<210> SEQ ID NO 19
<211> LENGTH: 24
<212> TYPE: DNA
<213> ORGANISM: Homo sapiens

<400> SEQUENCE: 19
aaaaattatc aaaaggaatt ttgg 24

<210> SEQ ID NO 20
<211> LENGTH: 25
<212> TYPE: DNA

-continued

<213> ORGANISM: Homo sapiens

<400> SEQUENCE: 20
ttactcttag tgaagagaca aacgc 25

<210> SEQ ID NO 21
<211> LENGTH: 36
<212> TYPE: DNA
<213> ORGANISM: Homo sapiens

<400> SEQUENCE: 21
agctgcggcc gcggtctgcg gcttaggtga aaatgc 36

<210> SEQ ID NO 22
<211> LENGTH: 36
<212> TYPE: DNA
<213> ORGANISM: Homo sapiens

<400> SEQUENCE: 22
agctgcggcc gcaaaacaaa gaaaaggaaa tctggt 36

<210> SEQ ID NO 23
<211> LENGTH: 37
<212> TYPE: DNA
<213> ORGANISM: Homo sapiens

<400> SEQUENCE: 23
agctgcggcc gcaagtgatg ccaccaaaaa gaaatga 37

<210> SEQ ID NO 24
<211> LENGTH: 36
<212> TYPE: DNA
<213> ORGANISM: Homo sapiens

<400> SEQUENCE: 24
agctgcggcc gctggaagga aacactgaaa taagaa 36

<210> SEQ ID NO 25
<211> LENGTH: 10
<212> TYPE: PRT
<213> ORGANISM: Homo sapiens

<400> SEQUENCE: 25

Glu Gln Lys Leu Ile Ser Glu Glu Asp Leu
1 5 10

<210> SEQ ID NO 26
<211> LENGTH: 33
<212> TYPE: DNA
<213> ORGANISM: Homo sapiens

<400> SEQUENCE: 26
gatggatccg gtctgcggct taggtgaaaa tgc 33

<210> SEQ ID NO 27
<211> LENGTH: 60
<212> TYPE: DNA
<213> ORGANISM: Homo sapiens

<400> SEQUENCE: 27
gatggatcct tagaggtctt cttctgagat gagcttctgc tccttctgga ctctctttct 60

<210> SEQ ID NO 28

-continued

<211> LENGTH: 33
<212> TYPE: DNA
<213> ORGANISM: Homo sapiens

<400> SEQUENCE: 28
gatggatcca gtgatgccac caaaaagaaa tga 33

<210> SEQ ID NO 29
<211> LENGTH: 60
<212> TYPE: DNA
<213> ORGANISM: Homo sapiens

<400> SEQUENCE: 29
gatggatcct tagaggtctt cttctgagat gagcttctgc tcgagaaaaa ataaagcaag 60

<210> SEQ ID NO 30
<211> LENGTH: 31
<212> TYPE: DNA
<213> ORGANISM: Homo sapiens

<400> SEQUENCE: 30
gatggatccc catgcctcgt gtaaaagcag c 31

<210> SEQ ID NO 31
<211> LENGTH: 31
<212> TYPE: DNA
<213> ORGANISM: Homo sapiens

<400> SEQUENCE: 31
gatggatccc ccaaagaaaa ggaaatctgg t 31

<210> SEQ ID NO 32
<211> LENGTH: 31
<212> TYPE: DNA
<213> ORGANISM: Homo sapiens

<400> SEQUENCE: 32
gatggatccc catgccacca aaaagaaatg a 31

<210> SEQ ID NO 33
<211> LENGTH: 31
<212> TYPE: DNA
<213> ORGANISM: Homo sapiens

<400> SEQUENCE: 33
gatggatccc cacaacattt cggtgaagag c 31

<210> SEQ ID NO 34
<211> LENGTH: 29
<212> TYPE: DNA
<213> ORGANISM: Homo sapiens

<400> SEQUENCE: 34
ccttgtgttg tatgggtgga acccagtga 29

<210> SEQ ID NO 35
<211> LENGTH: 31
<212> TYPE: DNA
<213> ORGANISM: Homo sapiens

<400> SEQUENCE: 35
acaccacgat gcctggagca atggcaacaa c 31

-continued

```
<210> SEQ ID NO 36
<211> LENGTH: 25
<212> TYPE: PRT
<213> ORGANISM: Homo sapiens

<400> SEQUENCE: 36

Met Leu Pro Glu Ser Glu Asp Glu Glu Ser Tyr Asp Thr Glu Ser Glu
 1               5                  10                  15

Phe Thr Glu Phe Thr Glu Asp Glu Leu
            20                  25


<210> SEQ ID NO 37
<211> LENGTH: 19
<212> TYPE: PRT
<213> ORGANISM: Homo sapiens

<400> SEQUENCE: 37

Cys Gln Thr Glu Glu Ala Ile Gln Thr Arg Ser Arg Thr Arg Lys Arg
 1               5                  10                  15

Val Gln Lys
```